(12) United States Patent
Takagi et al.

(10) Patent No.: US 6,325,781 B1
(45) Date of Patent: Dec. 4, 2001

(54) PUNCTURING DEVICE

(75) Inventors: Hiroshi Takagi; Hitoshi Suzuki, both of Yokohama; Kentaro Takemae, Kawasaki, all of (JP)

(73) Assignee: Mitsubishi Pencil Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/412,722

(22) Filed: Oct. 5, 1999

(30) Foreign Application Priority Data

| Oct. 20, 1998 | (JP) | ................................................ 10-315345 |
| Feb. 23, 1999 | (JP) | ................................................ 11-044034 |
| Feb. 23, 1999 | (JP) | ................................................ 11-044301 |
| Jun. 29, 1999 | (JP) | ................................................ 11-183138 |

(51) Int. Cl.$^7$ ..................................................... A61M 5/32
(52) U.S. Cl. ............... 604/198; 604/164.08; 604/164.12
(58) Field of Search ..................... 604/110, 192, 604/195, 197, 198, 263, 162, 164.04, 164.08, 164.12, 165.01, 170.03

(56) References Cited

U.S. PATENT DOCUMENTS

| 4,068,659 | 1/1978 | Moorehead . |
| 4,747,831 | 5/1988 | Kulli . |
| 4,813,940 | 3/1989 | Parry . |
| 4,917,669 | 4/1990 | Bonaldo . |
| 4,944,725 | 7/1990 | McDonald . |
| 4,950,252 | 8/1990 | Luther et al. . |
| 5,120,319 | 6/1992 | Van Heugten et al. . |
| 5,205,829 | 4/1993 | Lituchy . |
| 5,462,533 | 10/1995 | Daugherty . |
| 5,498,245 | * 3/1996 | Whisson ................................ 604/198 |
| 5,501,675 | 3/1996 | Erskine . |
| 5,573,510 | 11/1996 | Isaacson . |
| 5,575,777 | 11/1996 | Cover et al. . |
| 5,676,658 | 10/1997 | Erskine . |
| 5,690,619 | 11/1997 | Erskine . |
| 5,697,907 | 12/1997 | Gaba . |
| 5,700,250 | 12/1997 | Erskine . |
| 5,702,367 | 12/1997 | Cover et al. . |
| 5,749,860 | 5/1998 | Kyte . |
| 5,865,806 | 2/1999 | Howell . |
| 5,997,507 | * 12/1999 | Dysarz ..................... 604/164.12 X |

FOREIGN PATENT DOCUMENTS

Hei 10-15074   6/1998   (JP) .

* cited by examiner

Primary Examiner—Anhtuan T. Nguyen
(74) Attorney, Agent, or Firm—Darby & Darby

(57) ABSTRACT

A medical puncturing device for a so-called indwelling needle, includes: an indwelling needle composed of an indwelling outer needle element of a soft synthetic resin capillary tube and a puncturing inner needle element of a metallic capillary tube fitted through the outer needle element; and an outer sleeve for incorporating the indwelling needle. The indwelling needle has a projected part on the periphery at the rear end thereof while the outer sleeve has a guide slot cut along the axial direction on the peripheral surface thereof. The projected part is fitted through the guide slot and can move forward and backward so as to project and retract the indwelling needle with respect to the front side of the outer sleeve. The device further has locking arrangements in the front and rear ends of the guide slot so as to keep the indwelling needle at the projected and retracted positions.

10 Claims, 28 Drawing Sheets

//PUNCTURING DEVICE

BACKGROUND OF THE INVENTION

(1) Field of the Invention

The present invention relates to a puncturing device for an indwelling needle which provides for the prevention of health care workers from catching viruliferous infections such as AIDS, HIV or the like due to needlestick injuries from injectors.

(2) Description of the Related Art

In conventionally hospitals and other medical fields, the current main trend is to instruct medical workers not to recap the needle. Because of many needlestick injuries have occurred when a used injector is recapped. However, medical treatments such as blood collection, intravenous administration of medicament etc., are done, instead of treatment rooms, clinics and the like, at bed sites in sickrooms where equipment for collecting needles and injectors is not always provided for. In these cases, an optimal method for avoiding needlestick injuries is to recap the needle. No other devices which offer a worthwhile advantage for their adoption have been developed.

In a conventional indwelling needle which has an inner and outer needle, they are usually joined fast in order to avoid easy removal. Therefore, it is necessary to pull out the inner needle whilst appropriately pressing the outer needle after vain puncture or the like. So, this conventional configuration has the risk of an unskilled worker accidentally and erroneously pulling out the outer altogether with the inner needle from the vein or at least has the problem of producing strain on the vein, thus a solution has been needed. Further, it is necessary to proceed cautiously when the needle is placed into a weak thin vein of a child or the like. Specifically, there is a risk of the opposing wall of the lumen of the vein being damaged if the puncture is too deep. On the other hand, there is another problem in that a too shallow puncture cannot place the outer needle correctly even though the inner needle has punctured the vein.

SUMMARY OF THE INVENTION

The present invention relates to a device which allows health care workers to perform instant and safe disposal of the inner needle made up of a metallic injection needle etc., at once after use of an indwelling needle.

It is therefore an object of the invention to provide a puncturing device which protects health care workers from needlestick injuries from the needle (the inner needle made up of metal) after use.

It is another object of the invention to provide a puncturing device in which an indwelling needle can be fastened without any instability to reduce the burden on the human body during usage and which can prevent the needle from accidentally projecting out as well as preventing the re-use of the needle after it has been used once.

It is still another object of the invention to provide a puncturing device which is readily assembled and inexpensive and can be safely and correctly placed into a weak thin vein of a child etc.

In order to achieve the above objects, the present invention is configured as follows:

In accordance with the first aspect of the invention, a medical puncturing device for an indwelling needle, includes:

an indwelling needle composed of an indwelling outer needle element of a soft synthetic resin capillary tube and a puncturing inner needle element of a metallic capillary tube fitted through the outer needle element;

an outer sleeve for incorporating the indwelling needle and having a guide slot cut along the axial direction on the peripheral surface thereof;

an actuator disposed at the rear end of the indwelling needle and having a projected actuator part fitted through the guide slot; and a spring interposed between the rear end of actuator and the rear end of the outer sleeve for urging the indwelling needle to the retracted position inside the outer sleeve, and is characterized in that the indwelling needle can move in and out through the opening of the outer sleeve by the actuation of the actuator; and the guide slot further has an engagement window formed continuous from the proximity of the front end thereof forming an L-shape configuration; and the indwelling needle is kept in the projected state with respect to the outer sleeve when the actuator is moved forward and the projected actuator part formed on the actuator is turned so as to be engaged with the engagement window.

In accordance with the second aspect of the invention, a puncturing device for an indwelling needle composed of an indwelling outer needle element of a soft synthetic resin capillary tube and a puncturing inner needle of a hard capillary tube fitted through the outer needle element, includes:

the outer needle element disposed at the front end of the outer sleeve;

the inner needle fitted through the outer needle element;

an actuator integrally formed at the rear end of the inner needle and arranged inside the outer sleeve and the actuator having a projected actuator part; and an outer sleeve having a guide slot cut along the axial direction on the peripheral surface thereof and an engagement window formed continuous from the proximity of the front end thereof forming an L-shape configuration, the projected actuator part being fitted through the guide slot, and is characterized in that the tip of the inner needle is kept in the projected state from the tip of the outer needle element when the projected actuator part is engaged with the engagement window.

In accordance with the third aspect of the invention, the puncturing device having the above first or second aspect is characterized in that the actuator part is turned and slidably fitted into the engagement window so as to be engaged therein and in the engaged state, one end of the actuator part is mated with one end of the engagement window forming a disengageable engagement which prevents easy removal of the actuator part from the engagement window.

In accordance with the fourth aspect of the invention, the puncturing device having the above first or second aspect is characterized in that the outer sleeve has front and rear engagement windows in L-shaped configurations, one continuous from the proximity of the front end thereof and the other continuous from the proximity of the rear end thereof, and the actuator part is slidably fitted into each engagement window and engaged therein as the actuator part is turned.

In accordance with the fifth aspect of the invention, the puncturing device having the above first or second aspect is characterized in that when the projected actuator part is turned and engaged with the engagement window, abutment portions formed on the inner periphery of the outer sleeve and on the outer periphery of the actuator engage with each other so as to secure the actuator relative to the outer sleeve to thereby fix the indwelling needle without instability.

In accordance with the sixth aspect of the invention, the puncturing device having the above fourth aspect is characterized in that when the actuator part is engaged with the rear engagement window, an engaging portion formed at one end of the rear engagement window engages the actuator part so as to prohibit the actuator part from disengaging from the engagement window.

In accordance with the seventh aspect of the invention, the puncturing device having the above second aspect is characterized in that a spring urging the inner needle to the retracted position inside the outer sleeve is provided between the rear end of actuator and the rear end of the outer sleeve.

In accordance with the eighth aspect of the invention, the puncturing device having the above first or seventh aspect is characterized in that the spring which exerts twisting force on the actuator so that the actuator turns in the rotational direction is provided between the rear end of actuator and the rear end of the outer sleeve, and the actuator is automatically fitted and engaged into the rear engagement window due to the twisting force of the spring when the actuator moves back to the retracted position.

In accordance with the ninth aspect of the invention, the puncturing device having the above second aspect, further includes a rotation stopper between the front end of the outer sleeve and the rear end of the outer needle element.

In accordance with the tenth aspect of the invention, a puncturing device for an indwelling needle composed of an indwelling outer needle element of a soft synthetic resin capillary tube and a puncturing inner needle of a hard capillary tube fitted through the outer needle element, includes:

an outer sleeve having a guide slot cut along the axial direction on the peripheral surface thereof and an engagement window formed continuous from the proximity of the front end thereof forming an L-shape configuration;

the outer needle element disposed inside the outer sleeve;

the inner needle fitted through the outer needle element; and a actuator integrally formed at the rear end of the inner needle and having an actuator part, and is characterized in that the indwelling needle is kept in the projected state when the actuator part of the actuator is engaged with the engagement window at the front end, and the outer needle is advanced relative to the inner needle while the inner needle is retracted together with the actuator into the outer sleeve when the actuator part is turned from the L-shaped engagement window to the guide slot side.

In accordance with the eleventh aspect of the invention, the puncturing device having the above tenth aspect is characterized in that a movable ring which can move only in the axial direction with respect to the outer sleeve is arranged at the front opening of the outer sleeve and in front of the actuator while cam portions are formed on the movable ring and on the actuator, and when the actuator is turned, the movable ring moves forward so that its front end urges the rear end of the outer needle element to advance the outer needle element.

In accordance with the twelfth aspect of the invention, the puncturing device having the above tenth aspect is characterized in that when the outer needle is advanced with respect to the inner needle, the tip of the outer needle covers the beveled cutting edge of the inner needle.

DESCRIPTION OF THE PREFERRED EMBODIMENTS (The First Embodiment)

Figure 1:
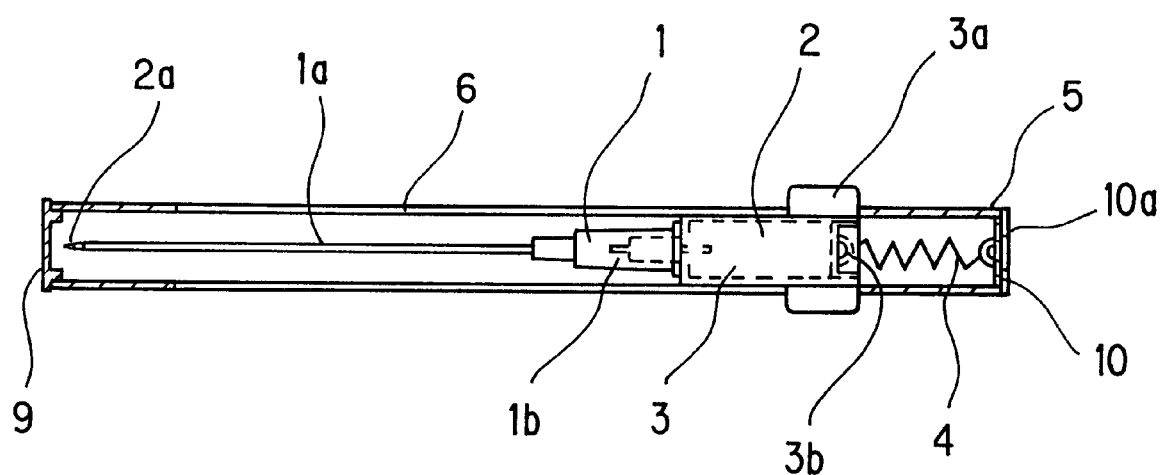
FIG. 1 is a sectional view with partial non-sectional representation showing an unused state of a puncturing device in accordance with the first embodiment of the invention, where an indwelling needle is contained in an outer sleeve and locked in the unusable condition.

FIG. 1 is a sectional view showing an unused state of a puncturing device of the invention, where an indwelling needle is contained in an outer sleeve 5 and pulled in by a spring 4 to such a position that the needle tip will not touch a cap 9 while projections 3a are rotated and plunged into locking portions 8 (FIG. 2) so that the device is locked so as not to be used.

Figure 2:
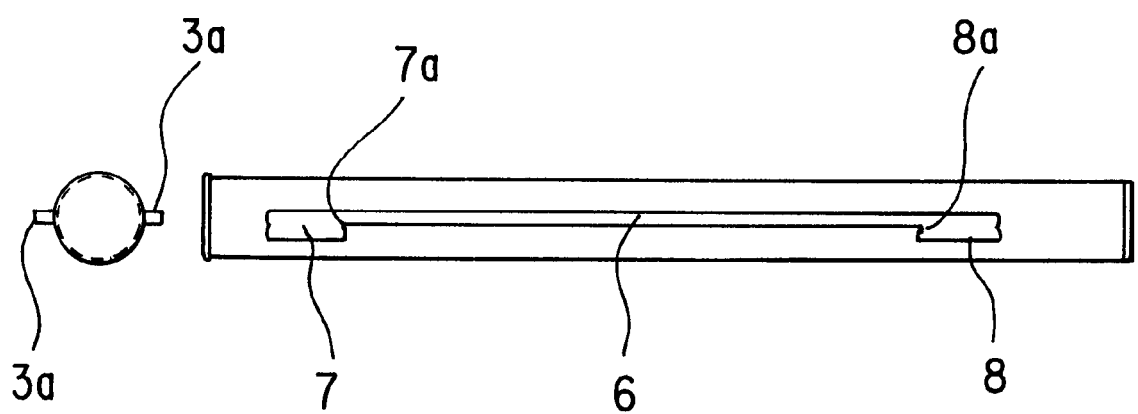
FIG. 2 is an external view of FIG. 1.

FIG. 2 is an external view of FIG. 1.

Figure 3:
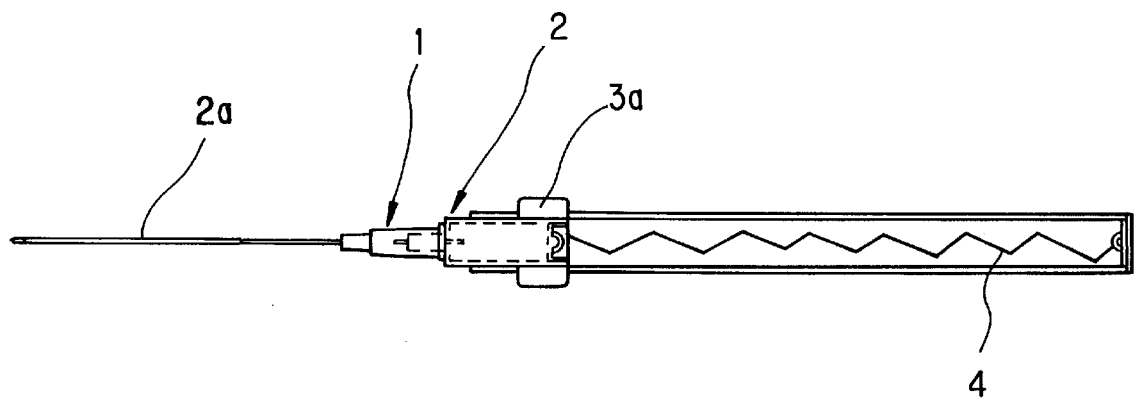
FIG. 3 is a sectional view showing a usable locked state where an indwelling needle is projected to be applied to the human body.

FIG. 3 is a sectional view showing a usable locked state where the above locked state is released and the incorporated indwelling needle is set by pushing out finger-held projections 3a to the predetermined position along guide slots 6 (FIGS. 1 and 2) provided for outer sleeve 5 and then rotating projections 3a so as that they are plunged into L-shaped locking portions 7 (FIG. 2) so that the device is locked for use. Since the needle is locked while being tensioned by spring 4, the needle will not sway during use and the outer sleeve is long enough to allow the operator's hand to hold it tightly, thus providing sufficient stability.

Figure 4:
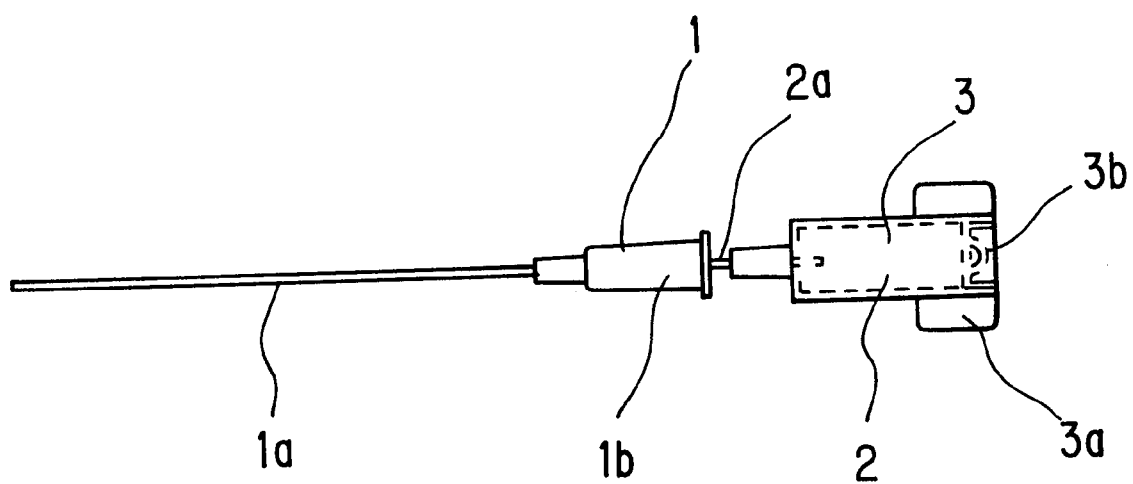
FIG. 4 is a view showing an indwelling needle configuration.

FIG. 4 is a view showing a configuration of an indwelling needle which is composed of an indwelling outer needle element 1 of a soft synthetic resin capillary tube and a puncturing inner needle element 2 of a metallic capillary tube fitted through outer needle element 1.

Figure 5:
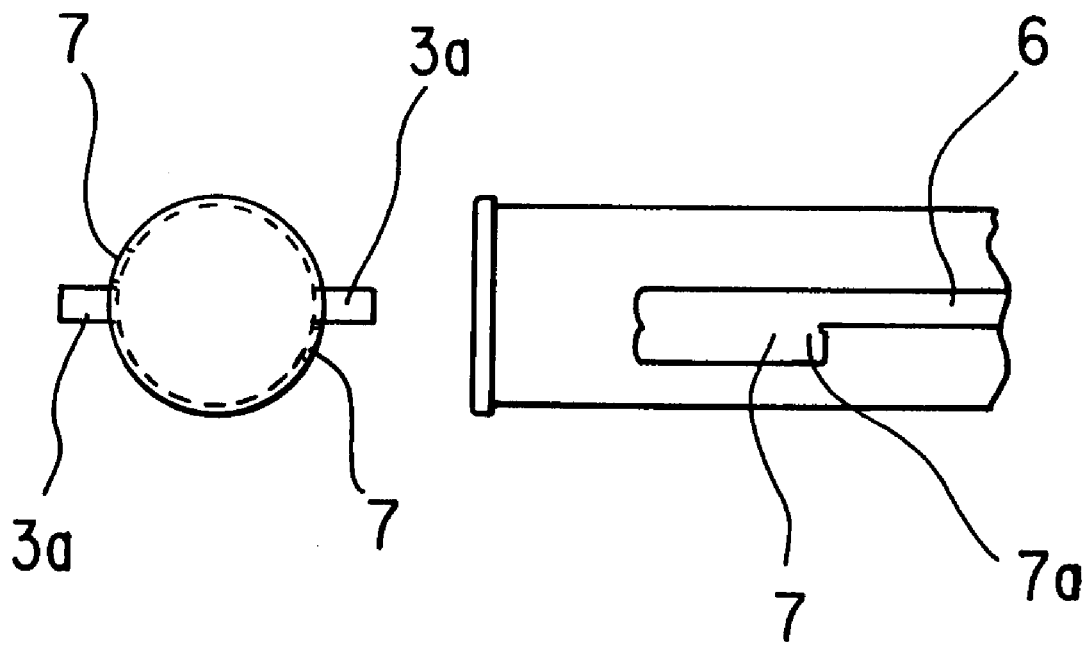
FIG. 5 is a view illustrating a locking portion.

FIG. 5 is an enlarged view of the area around locking portion 7 shown in FIG. 2, illustrating the positional relationship between projections 3a, guide slot 6 and locking portion 7.

Figure 6:
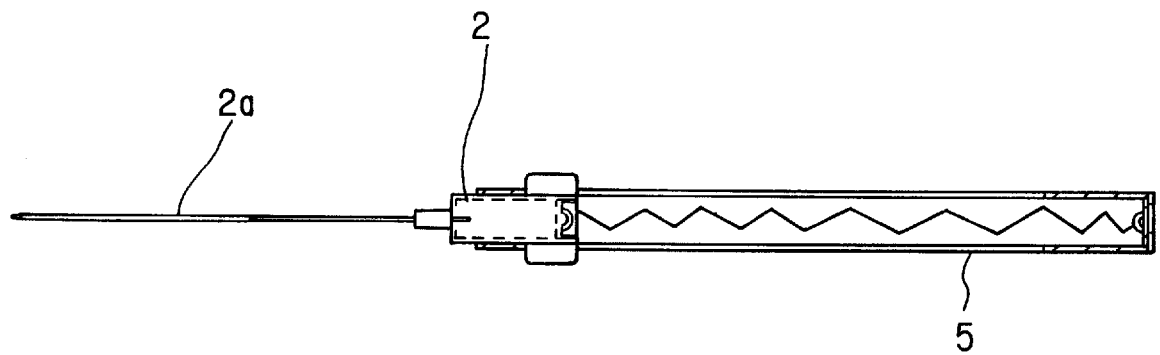
FIG. 6 is a sectional view with partial non-sectional representation showing a used state where only the inner needle element is present while the outer needle element has been left in the human body.

FIG. 6 is a sectional view showing the used state where only inner needle element 2 is present after being used and after the outer needle element has been left in the human body.

Figure 7:
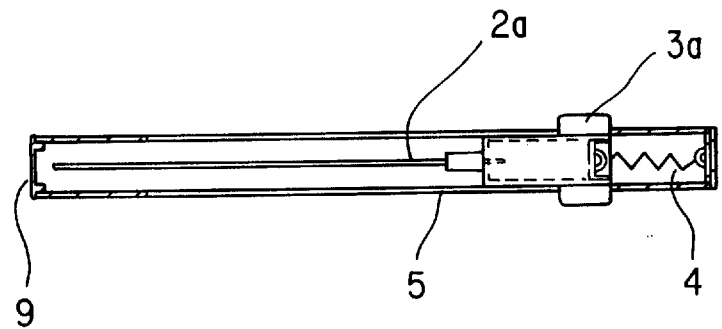
FIG. 7 is a sectional view with partial non-sectional representation showing a state where the inner needle is collected inside the outer sleeve by the function of a spring.

FIG. 7 is a view showing a state where projections 3 have been released from the locked state during use so that the inner needle is collected again inside outer sleeve 5 by the function of spring 4 and the projections are being locked into locking potions 8 (FIG. 2).

(The Operation of the First Embodiment)

With the puncturing device of this embodiment, metallic inner needle element 2 to be disposed of after insertion of outer needle element 1 into the human body can be collected instantly inside outer sleeve 5 by a single-hand operation by virtue of the restoring force of spring 4. In the stored state, the needle is pulled in, to a position that disallows the needle tip to touch cap 9, then projections 3a are rotated and plunged into locking portions 8 so that the device is locked so as not to be used. Therefore, the metallic inner needle element will not be damaged during transport of the product. Further, since this mechanism enables the needle to be pulled back by the spring after use and locked, it is possible to prevent the needle from being unintentionally protruded from the outer sleeve during the process of disposal and hence protect health care workers from the risk of needle-stick injuries.

The indwelling needle is set by pushing out projections 3a to the predetermined position along guide slots 6 formed in outer sleeve 5 then rotating projections 3a so as to be plunged into L-shaped locking portions 7 so that the device is locked for use. Further, the needle is locked by locking portions 7 as it is tensioned by spring 4. Therefore, the needle will not sway during use. Also, outer sleeve 5 is long enough to allow the operator's hand to hold it tightly, thus providing sufficient stability.

After use to the human body, the needle can be easily collected by releasing the lock by a single hand operation by the force of spring and, further, can be locked so as not to project out after collection.

(The Second Embodiment)

Figure 8:
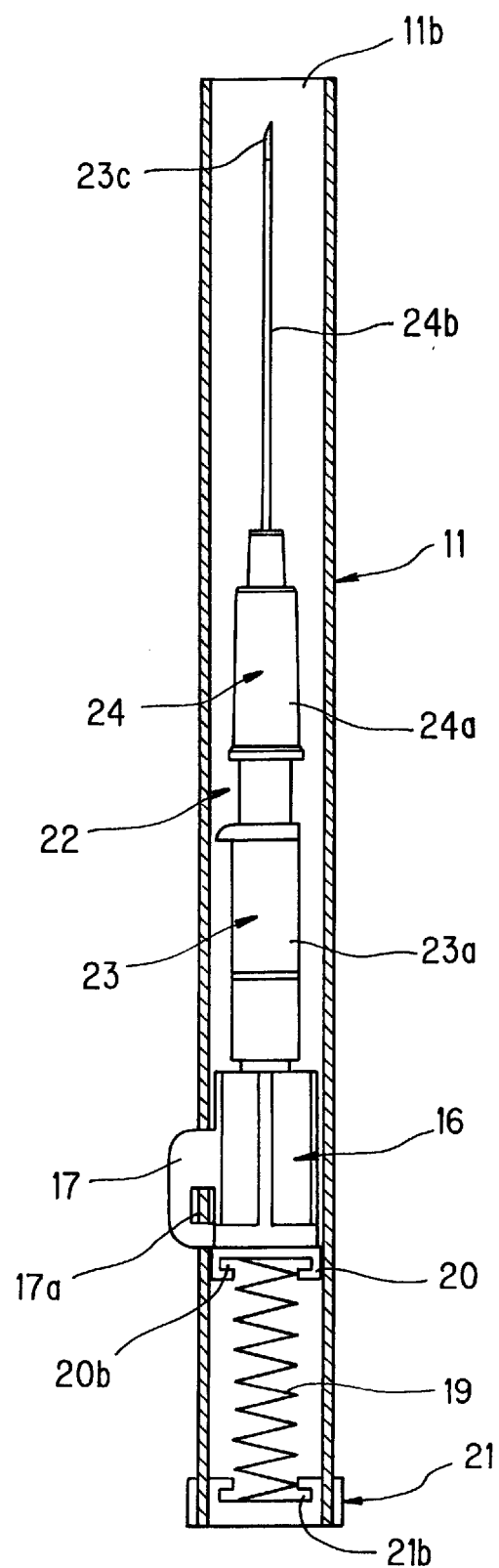
FIG. 8 is a sectional view with partial non-sectional representation showing an unused state of a puncturing device in accordance with the second embodiment of the invention, where an indwelling needle is contained in an outer sleeve.
Figure 9:
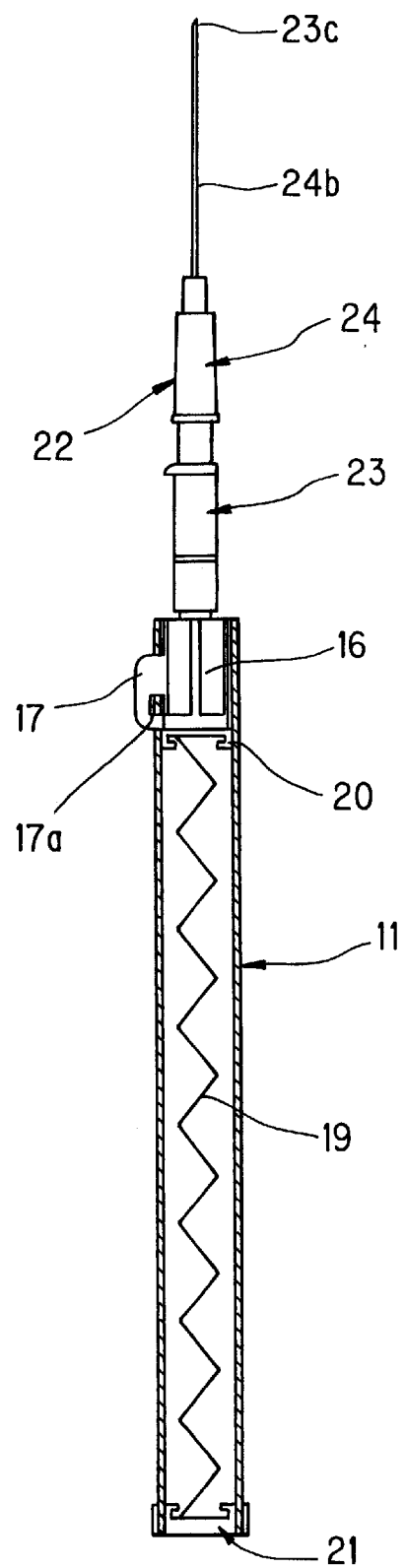
FIG. 9 is a sectional view showing a usable state where an indwelling needle is projected to be applied to the human body.

FIG. 8 is a view showing an unused state of a puncturing device of the second embodiment of the invention, where an indwelling needle 22 is pulled in by a spring 19 and contained in an outer sleeve 11. FIG. 9 is a view showing a usage state where indwelling needle 22 is projected from the front end of outer sleeve 11.

Figure 10:
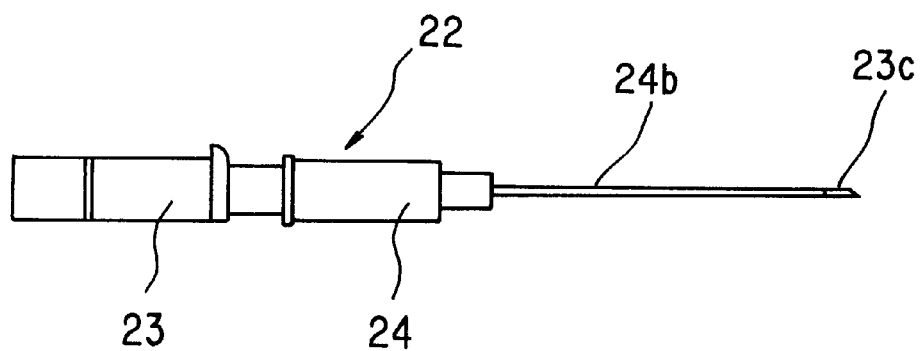
FIG. 10 is a view showing an indwelling needle configuration.
Figure 11:
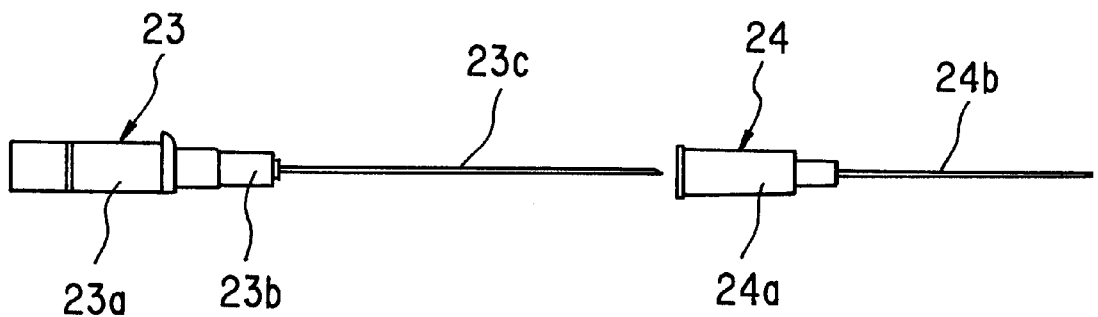
FIG. 11 is a view showing inner and outer needle elements of an indwelling needle.

FIGS. 10 and 11 show the configuration of indwelling needle 22.

Indwelling needle 22 comprises: an outer needle element 24 for indwelling composed of a base part 24a and a needle 24b of a soft synthetic resin capillary tube; and an inner needle element 23 composed of a base part 23a and an inner needle 23c of a metallic capillary tube. Needle 23c of inner needle element 23 is fitted through needle 24b of outer needle element 24 so that the tip of needle 23c is exposed appropriately from the tip of needle 24b while base part 24a of outer needle element 24 is fitted on a shank 23b of inner needle element 23.

Figure 12:
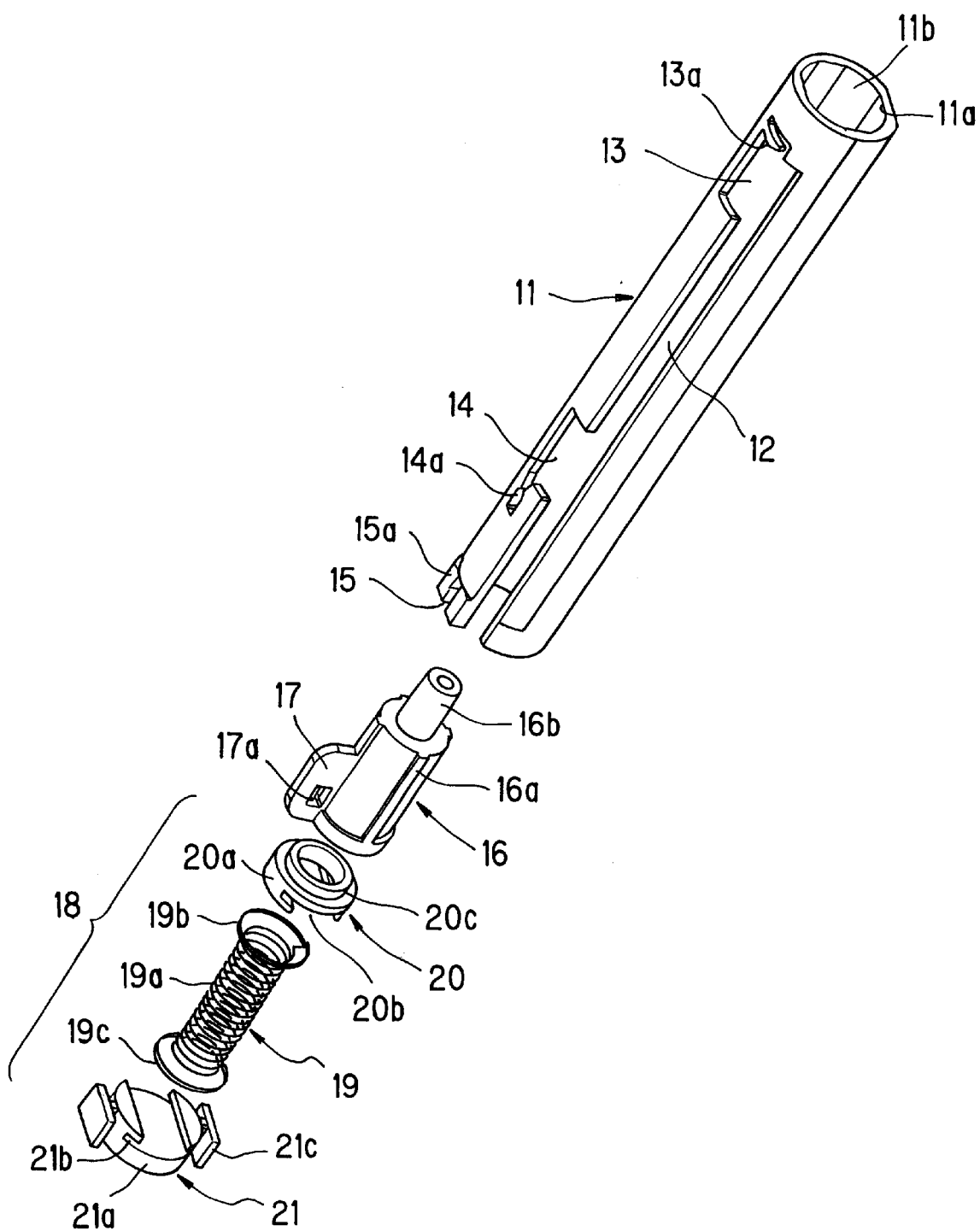
FIG. 12 is an exploded perspective view showing parts of a puncturing device (except an indwelling needle)

FIG. 12 is an exploded perspective view showing parts of the puncturing device of this embodiment.

Figure 15:
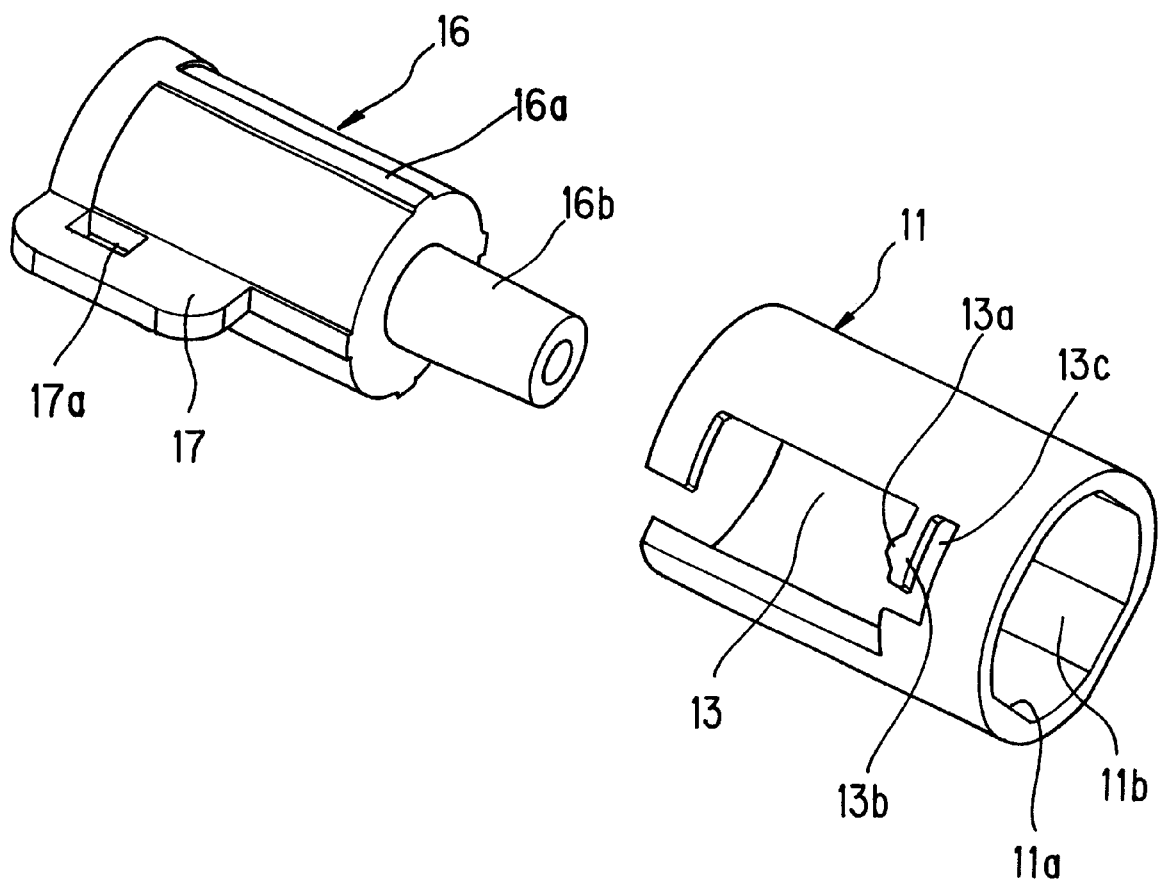
FIG. 15 is a perspective view showing the relationship between an actuator part in its forward position and an engagement window of an outer sleeve.

As seen in this figure, outer sleeve 11 has an elongated guide slot 12 formed on the peripheral surface thereof extending axially and opening to the rear. An engagement window 13 is formed continuous from the proximity of the front end of guide slot 12 so as to form an L-shape configuration. A resiliently deflectable piece 13b (FIG. 15) is formed by provision of a cut-in window 13c (FIG. 15) in the front part of engagement window 13. This deflectable piece 13b has an engaging part 13a projecting to the rear therefrom (see FIG. 15). There is another engagement window 14 which is also formed continuous from the rear of guide slot 12 so as to form an L-shape configuration. This engagement window 14 has an fitting slot 14a extending to the rear from the rear end thereof. The opposing sidewalls defining the opening of fitting slot 14a are formed with saw-toothed engaging projections 14b (see FIG. 19).

Formed on the rear outer peripheral portion of outer sleeve 11 are a pair of flat portions 15a (only one of them can be seen) which each has an engaging slot 15 having saw-toothed engaging projections. Flat portions 11a are formed on the inner peripheral side of outer sleeve 11, at appropriate sites running in the axial direction.

An actuator 16 is a tubular configuration having a passage hole at the axial center with ribs 16a formed on the outer periphery thereof at appropriate sites running in the axial direction. A projected actuator part 17 extending in the axial direction is formed on one side of the outer periphery of actuator 16. This projected actuator part 17 has a rectangular engagement window 17a cut and passing through the thickness thereof. Actuator 16 further has a cylindrical attachment part 16b at the front end thereof.

Figure 13:
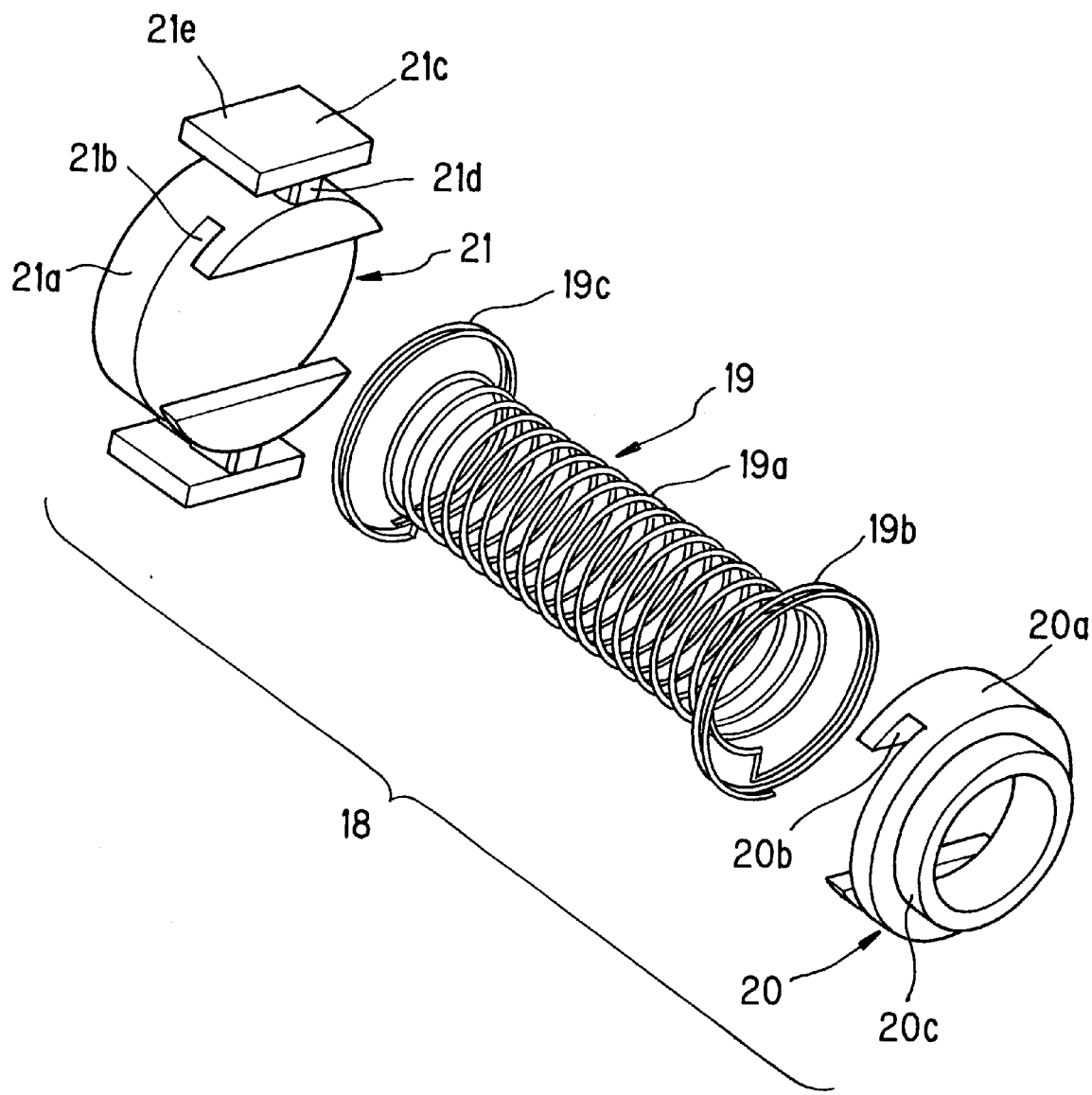
FIG. 13 is an exploded perspective view showing a spring mechanism.

A spring arrangement 18 is assembled of a spring 19, a stopper piece 20 and a tail plug 21 (see FIG. 13).

Spring 19 has a coil portion 19a in the middle portion thereof and a pair of coil end turns 19b and 19c at both ends thereof having an appropriately greater diameter than the coil portion 19a.

Engaging piece 20 is of a ring, and is composed of a rear cylindrical portion 20a and a front cylindrical portion 20c which is smaller in diameter than rear cylindrical portion 20a. Rear cylindrical portion 20a has an engaging groove portion 20b of a cutout running perpendicular to the axial direction and having an axial cross-section of T with its top facing forward.

Tail plug 21 also has an engaging groove portion 21b of a cutout running perpendicular to the axial direction and having an axial cross-section of T with its top facing rearward. Further, a pair of engaging portions 21c are provided on the cylindrical surface of tail plug 21 at right angles with engaging groove portion 21b. Each engaging portion 21c is formed of a rib 21d and a plate piece 21e, arranged in a T-shape.

In this configuration, the coil end turns formed at both ends of spring 19 are fitted into the corresponding engaging grooves of engaging piece 20 and tail plug 21, thus the engaging piece 20 and tail plug 21 are coupled at both ends of spring 19.

Figure 14:
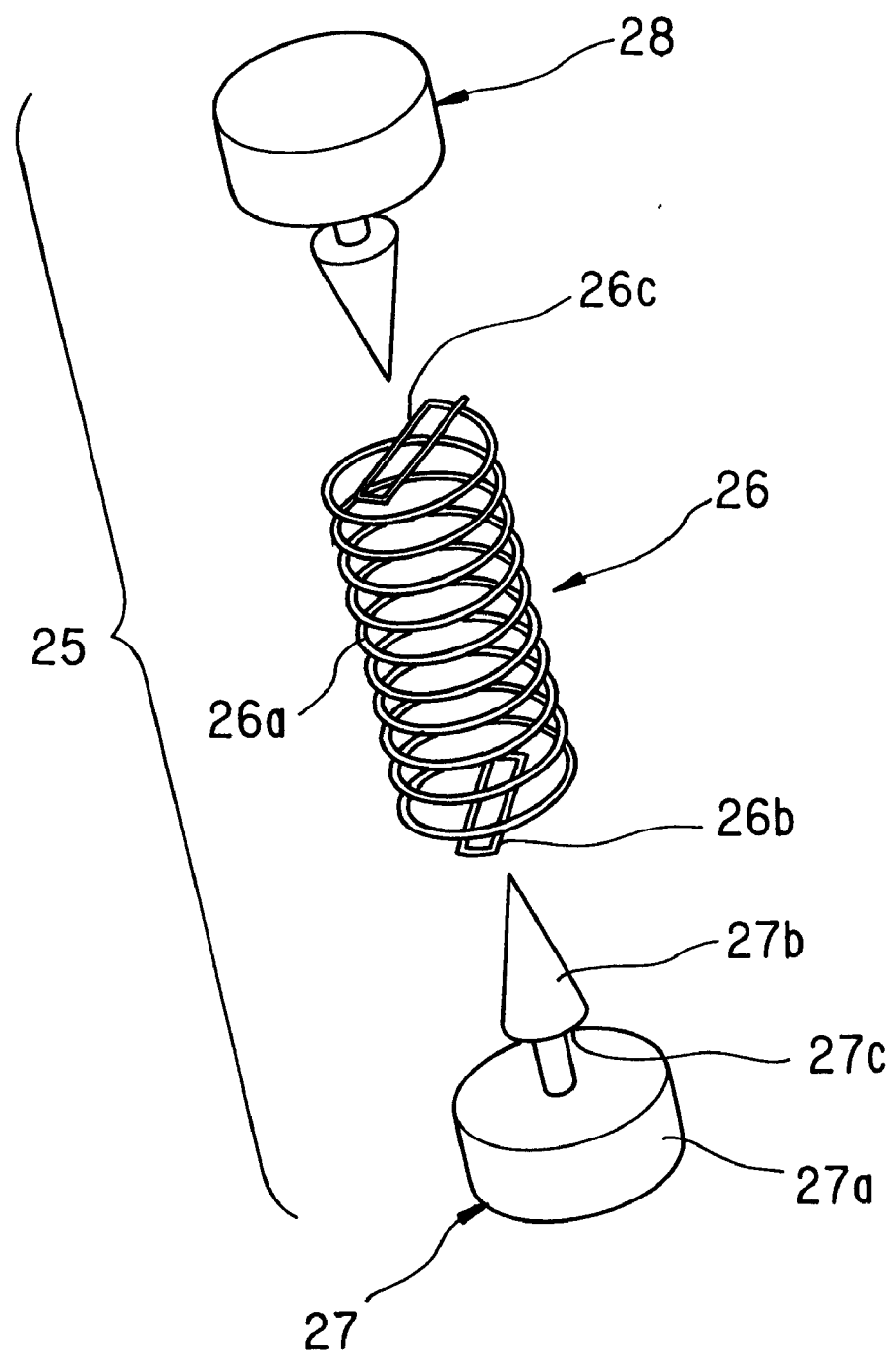
FIG. 14 is an exploded perspective view showing another embodiment of a spring mechanism.

FIG. 14 shows another spring assembly 25 as a variational embodiment, which is also assembled of a spring 26, an engaging piece 27 and a tail plug 28.

Spring 26 has a coil portion 26a in the middle portion thereof and a pair of flattened loop-shaped hooking portions 26b and 26c at both ends thereof.

Engaging piece 27 and tail plug 28 are basically of the same structure but may partially differ depending on the attachment conditions of the outer sleeve and the actuator. Here, assuming the same structure, engaging piece 27 will be described. A cylindrical portion 27a has a sagittate engaging portion 27b at its one end, which fits into and couples with hooking portion 26b of spring 26 as the front end of sagittate engaging portion 27b resiliently enlarges hooking portions 26b until hooking portion 26b engages the stepped portion 27c of engaging portion 27b.

Returning to the above spring assembly 18, the spring assembly 18 is joined by fixing cylindrical part 20c of engaging piece 20 to the rear end of actuator 16 (examples of fixing methods include press fitting, welding, bonding, screw fitting, and other joinings by using an engaging portion between the two elements). In this embodiment, two parts, or actuator 16 and engaging piece 20 are used to ensure assembly performance of the puncturing device and ease of formation of the elements, but the actuator and engaging piece may be integrally formed. Actuator 16 with spring assembly 18 joined thereto is inserted into the bore of outer sleeve 11 from the sleeve's rear end while ribs 21d of tail plug 21 fit into tail plug engaging slots 15 formed at the rear end of outer sleeve 11 so that ribs 21d are caught and fixed inside tail plug engaging slots 15. Though not illustrated in detail in the figure, both of the opposing sidewalls defining tail plug engaging slot 15 is formed with a saw-toothed projection defined by an inclined surface and a perpendicular surface. That is, the inclined surface of the projection is located on the insertion side of rib 21d (FIG. 13) of tail plug 21, and the rib 21d is inserted as it resiliently enlarges the tail plug engaging slot 15 until the rear end of the rib becomes engaged and fixed by the stepped portion defined by the perpendicular surface of the projection.

Figure 16:
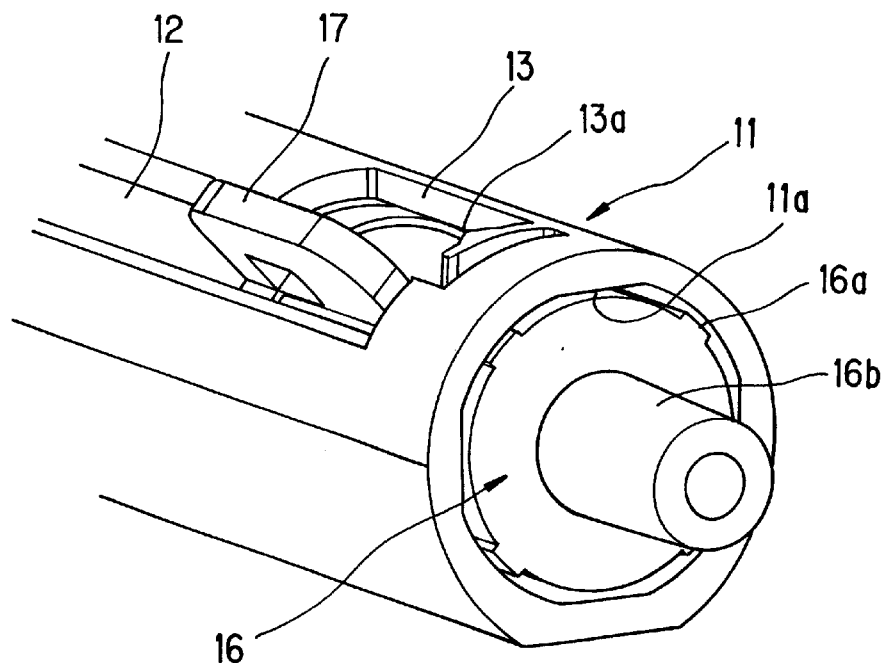
FIG. 16 is a partial perspective view showing a state where an actuator part is abutted on the front end of an guide slot of an outer sleeve immediately before the actuator part is slidably fitted into an engagement window.
Figure 17:
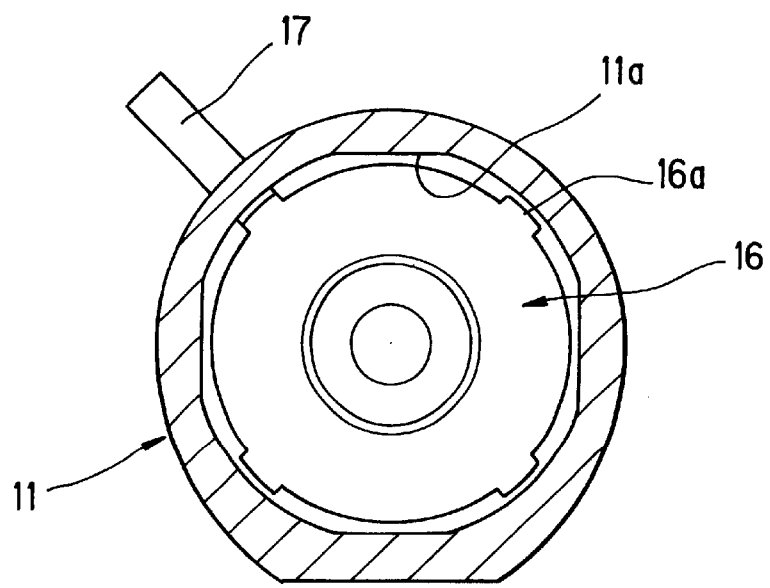
FIG. 17 is a view of that shown in FIG. 16 viewed from the front side of the outer sleeve.

Actuator part 17 of actuator 16 is fitted in, and projected outwardly from, guide slot 12 of outer sleeve 11 so that the actuator part 17 is slid forward by the fingers along guide slot 12. FIG. 16 shows the state where the actuator part 17 is abutting on the front end of guide slot 12. FIG. 17 shows the same state, viewed from the front side of the outer sleeve 11.

Figure 18:
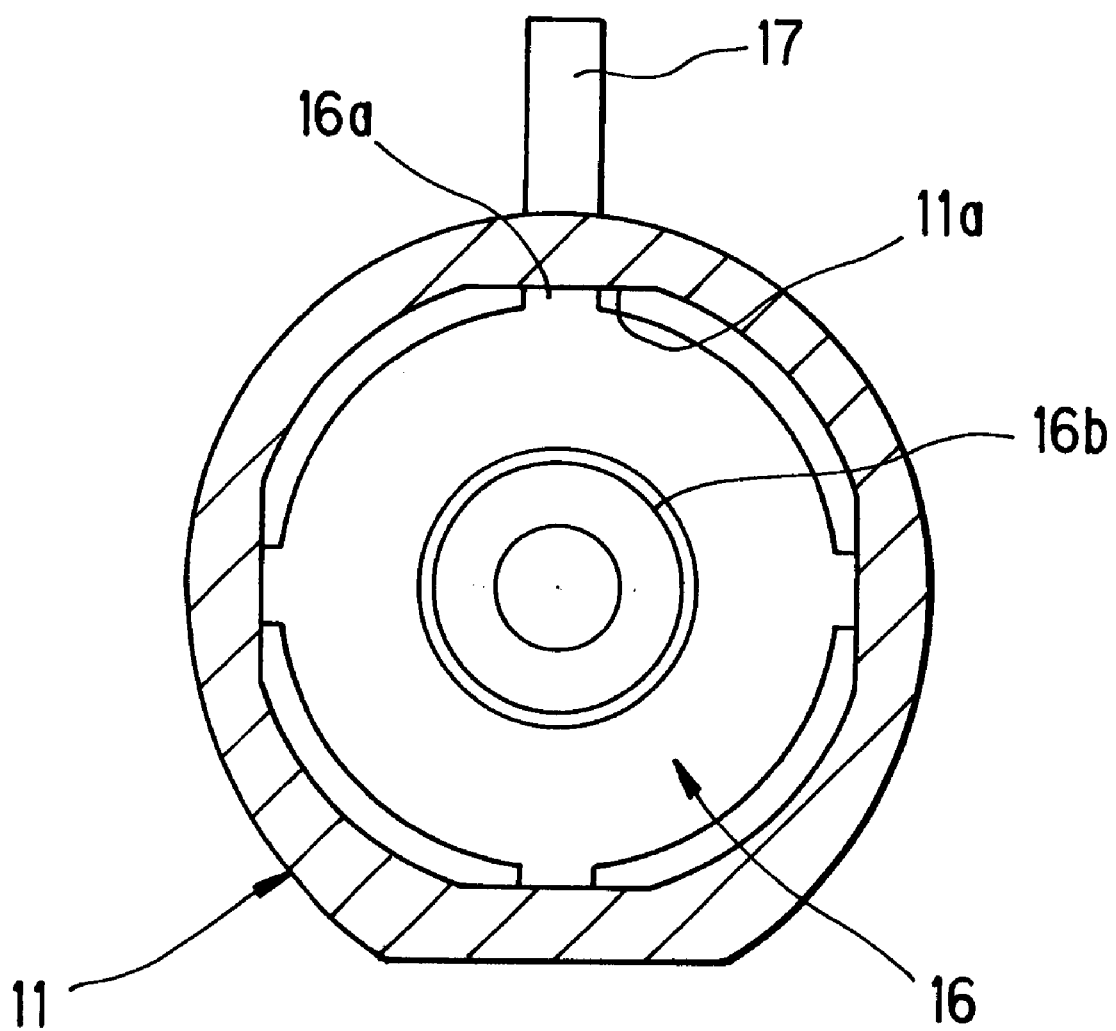
FIG. 18 is a view showing a state where an actuator part is rotated and slidably fitted into an engagement window.

FIG. 18 is a view showing the state, viewed from the front side of the outer sleeve 11, where actuator part 17 is rotated from the above state and slidably fitted into engagement window 13 of the outer sleeve 11.

As understood from comparison between FIGS. 17 and 18, in the case of FIG. 17, the outer peripheral portions of ribs 16a formed at appropriate sites on the outer periphery of actuator 16 are located an appropriate clearance away from the inner periphery of the outer sleeve 11 so that actuator 16 can slide. In contrast, in the case of FIG. 18, the outer peripheral portions of ribs 16a are in contact with flat portions 11a formed on the inner periphery of the outer sleeve 11 so that actuator 16 becomes fixed relative to outer sleeve 11 without instability. The means of abutment and engagement between the inner periphery of outer sleeve 11 and the outer periphery of the actuator part 17 when projected actuator part 17 is turned until it is engaged with engagement window 13 should not be limited to the above configuration but can be created by providing projections and grooves therebetween in an appropriate combination.

The state shown in FIG. 9 is that shown in FIG. 18 where indwelling needle 22 shown in FIG. 10 is attached to attachment part 16b of actuator 16. This state illustrates the usage state of the puncturing device as already stated above.
(The Operation of the Second Embodiment)

With the puncturing device of this embodiment, metallic inner needle element 23 to be disposed of after insertion of outer needle element 24 into the human body can be collected instantly inside outer sleeve 11 by a single hand operation by virtue of the restoring force of spring 19. That is, the collection can be done by only rotating actuator part 17 by the fingers relative to outer sleeve 11, up to the state shown in FIG. 16. In this state, inner needle element 23 is collected inside the outer sleeve 11 in the same manner as the unused state of the puncturing device shown in FIG. 8.

When, with actuator 16 retracted, actuator part 17 is turned so as to abut engagement window 14, the peripheral portions of ribs 16a abut on, and become engaged with, the flat portions formed on the inner periphery of the outer sleeve 11 so that actuator 16 will be fixed relative to outer sleeve 11 without instability, as in a similar manner to the case where actuator part 17 abuts engagement window 13 as stated above.

Figure 19:
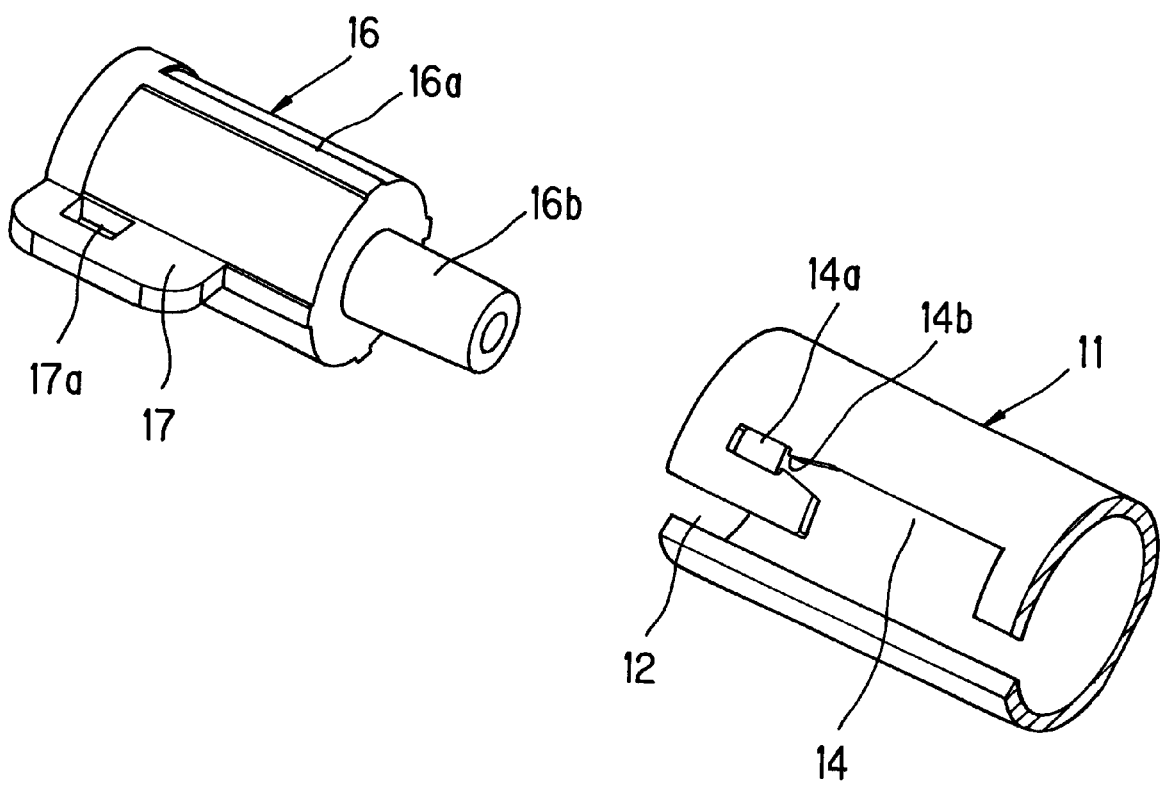
FIG. 19 is a perspective view showing the relationship between an actuator part in its retracted position and an engagement window of an outer sleeve.

In this state, when actuator part 17 is further moved back to fit into fitting slot 14a which is formed further behind engagement window 14, engaging projections 14b fit into the engagement window 17a cut through actuator part 17. That is, since fitting slot 14a has a pair of saw-toothed projections 14b as shown in FIG. 19, their perpendicular surfaces engage the rear end of engagement window 17a, thus prohibiting any attempted moving of actuator part 17 forward.
(The Third Embodiment)

Figure 20:
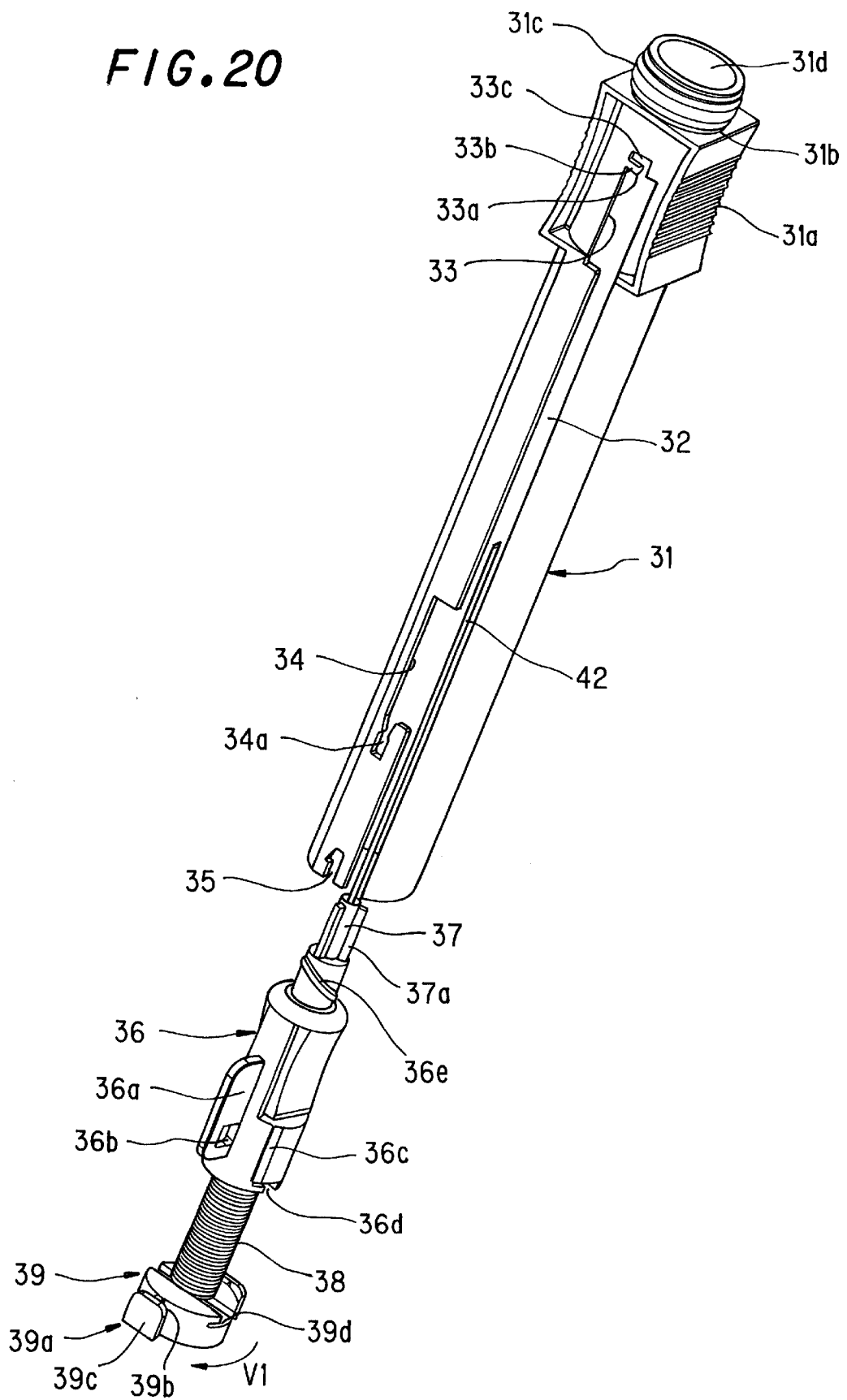
FIG. 20 is an exploded perspective view showing essential components of a puncturing device of the third embodiment of the invention.
Figure 21:
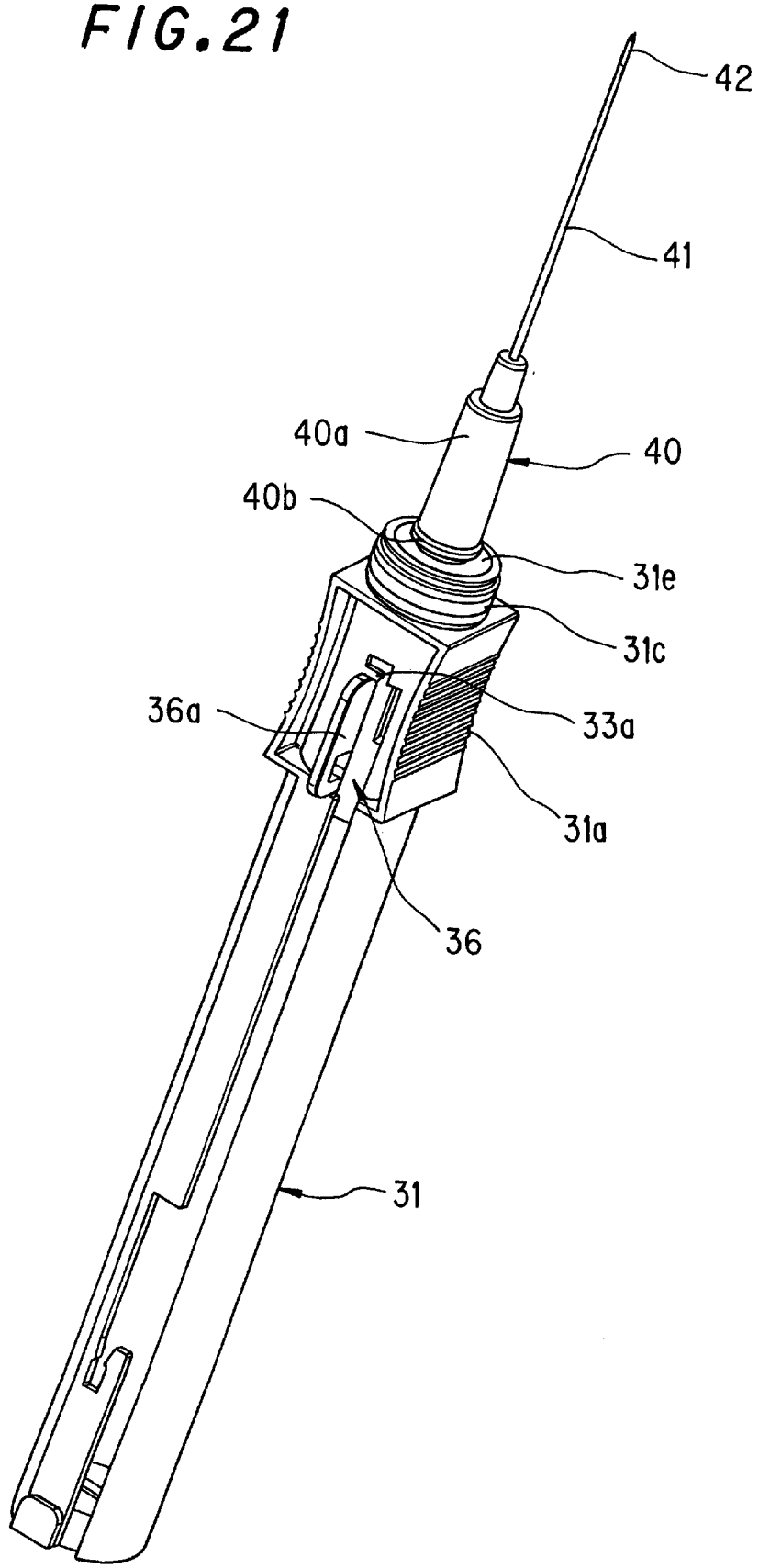
FIG. 21 is a perspective view showing a state of a puncturing device of the third embodiment immediately before its use.

FIGS. 20 through 23 are perspective views showing a puncturing device of the third embodiment of the invention. FIG. 21 shows an unused state of a puncturing device where an outer needle element 40 is mounted at the front end of an outer sleeve 31 by means of a movable ring 31e while an actuator part 36a of an actuator 36 is engaged with an engagement window 33 (FIG. 20) so as to keep the tip of an inner needle 42 projected from the tip of outer needle 41.

Here, the indwelling needle comprises: outer needle element 40 composed of a base part 40a and an outer needle 41 of a soft synthetic resin capillary tube; and an inner needle 42 of a hard, e.g., metal, capillary tube. Inner needle 42 is fitted through outer needle 41 of outer needle element 40 so that the tip of inner needle 42 is exposed appropriately from the tip of outer needle 41.

Further, as shown in FIG. 20, inner needle 42 is fixed to an attachment part 37 integrally formed at the front end of actuator 36. Ribs 37a are formed at appropriate sites on the outer periphery of attachment part 37 so that the outer peripheral portions of ribs 37a engage the inner periphery of a base part 40a (FIG. 21) of the outer needle element so that inner needle 42, hence actuator 36 can be attached so as not to easily drop off from outer needle element 40. Here, it is also possible to provide an attachment part 37 separately from actuator 36 so as to form a unit of an indwelling needle separated from the actuator and join the attachment part to the actuator.

Outer sleeve 31 has an elongated guide slot 32 formed on the peripheral surface thereof extending axially and opening to the rear. An engagement window 33 is formed continuous from the proximity of the front end of guide slot 32 so as to form an L-shape configuration. A resiliently deflectable piece 33b is formed by provision of a cut-in window 33c in the front part of engagement window 33. This deflectable piece 33b has an engaging part 33a projecting to the rear therefrom.

A rectangular shaped grip 31a is formed in the front part of outer sleeve 31. This grip 31a has a flat rim 31b on the same side as engagement window 33. Further, an attachment part 31c is formed in the front end of grip 31a and an opening 31d is formed in the center of attachment part 31c.

Provided inside an opening 31d is a movable ring 31e (FIG. 21) which moves in only the axial direction with respect to outer sleeve 31, being limited by the combination of ribs and grooves formed therebetween. Movable ring 31e is preferably prevented from falling out from opening 31d. This means can be easily attained so that description is omitted.

The bore of movable ring 31e is formed with an unillustrated spiral cam portion which will engage an aftermentioned spiral cam portion 36e formed on actuator 36.

There is another engagement window 34 which is also formed continuous from the rear of guide slot 32 so as to form an L-shape configuration. This engagement window 34 has an fitting slot 34a extending to the rear from the rear end thereof. The opposing sidewalls defining the opening of fitting slot 34a are formed with saw-toothed engaging projections.

Formed on the rear peripheral portion of outer sleeve 31 are a pair of flat portions (only one of them can be seen) which each has an engaging slot 35 having saw-toothed engaging projections.

Actuator 36 has a cylindrical portion at the front part thereof with spiral cam portion 36e formed on the outer periphery of the cylindrical portion. Attachment part 37 having ribs 37a at appropriate sites on the outer periphery thereof are formed further to the front of the cylindrical portion.

Actuator 36 further has ribs 36c at appropriate sites in the rear cylindrical portion having a slightly greater diameter and a projected actuator part 36a extending in the axial direction, on one side on the outer periphery thereof. This projected actuator part has a rectangular engagement window 36b cut and passing through the thickness thereof.

Actuator 36 further has an attachment groove 36d at the rear end thereof for fixing the front end of a spring 38.

With this configuration, when actuator part 36b of actuator is turned, cam portion 36e engages the cam portion formed on movable ring 31e (FIG. 21) and moves movable ring 31e forward.

A tail plug 39 has an attachment groove 39d at the front cylindrical end thereof for fixing the rear end of spring 38. This attachment groove has a similar structure to attachment groove 36d formed at the rear end of actuator 36.

Further, provided on the peripheral surface of the cylindrical portion of the tail plug are a pair of engaging portions 39a, each of which is formed of a rib 39b and a plate piece 39c, arranged in a T-shape.

With this arrangement, actuator 36 and tail plug 39 are coupled at both ends of spring 38.

Actuator 36 and tail plug 39 joined by spring 38 is inserted into the bore of outer sleeve 31 from the sleeve's rear end so that ribs 39b of tail plug 39 fit into engaging slots 35 formed at the rear end of outer sleeve 31 and ribs 39b are caught and fixed inside tail plug engaging slots 35. Though not illustrated in detail in the figure, either of the opposing sidewalls defining engaging slot 35 is formed with a saw-toothed projection defined by an inclined surface and a perpendicular surface. That is, the inclined surface of the projection is located on the insertion side of rib 39b of tail plug 39, and as the rib is inserted it resiliently enlarges the engaging slot until the rear end of the rib becomes engaged and fixed by the stepped portion defined by the perpendicular surface of the projection.

Actuator part 36a of actuator 36 is fitted in, and projected outwardly from, guide slot 32 of outer sleeve 31 so that actuator part 36a is slid forward by the fingers along guide slot 32. When actuator part 36a is turned while actuator part 36a being abutted on the front end of guide slot 32, it is slidably fitted into engagement window 33 of the outer sleeve. At the same time, engaging part 33a engages and fixes actuator part 36a so as to prevent it from easily rotating and disengaging from engagement window 33.

When the outer peripheral portions of ribs 36c formed at appropriate sites on the rear outer periphery of actuator 36 are located an appropriate clearance away from the inner periphery of outer sleeve 31, the actuator can slide. In contrast, when actuator part 36a is slidably fitted into engagement window 33 of the outer sleeve, the outer peripheral portions of ribs 36c are in contact with flat portions (not shown) formed on the inner periphery of outer sleeve 31 so that actuator 36 becomes fixed relative to outer sleeve 31 without instability.

The means of the engagement between the inner periphery of the outer sleeve and the outer periphery of the actuator when the projected actuator part is turned until it is engaged with the engagement window should can be created by providing projections and grooves therebetween in an appropriate combination.

Upon insertion of actuator 36 into outer sleeve 31, tail plug 39 may be turned in the direction indicated by the arrow V1 and fixed to the rear end of outer sleeve 31 after fitting actuator part 36a into guide slot 32, so as to allow spring 38 to exert a twisting force in the rotational direction. By this setting, when actuator 36 is moved backward and positioned at engagement window 34, actuator part 36a will automatically fit into engagement window 34 by virtue of the restoring force or the twisting force of spring 38. The strength of this twisting force can be adjusted as appropriate by changing the rotated angle of tail plug 39 in such a range that the actuator part 36a will not come off easily due to touch, vibration and other interference during handling.

This configuration not only provides simple handling but also can eliminate the necessity of an engaging portion for avoiding easy removal of the actuator part from the engagement window.

Referring to FIG. 21, outer needle element 40 is mounted to an attachment 31c at the front end of outer sleeve 31 with inner needle 42 inserted therethrough. A cap 43 is added and covers outer needle element 40 and is fixed to attachment 31c as shown in FIG. 22.

Figure 22:
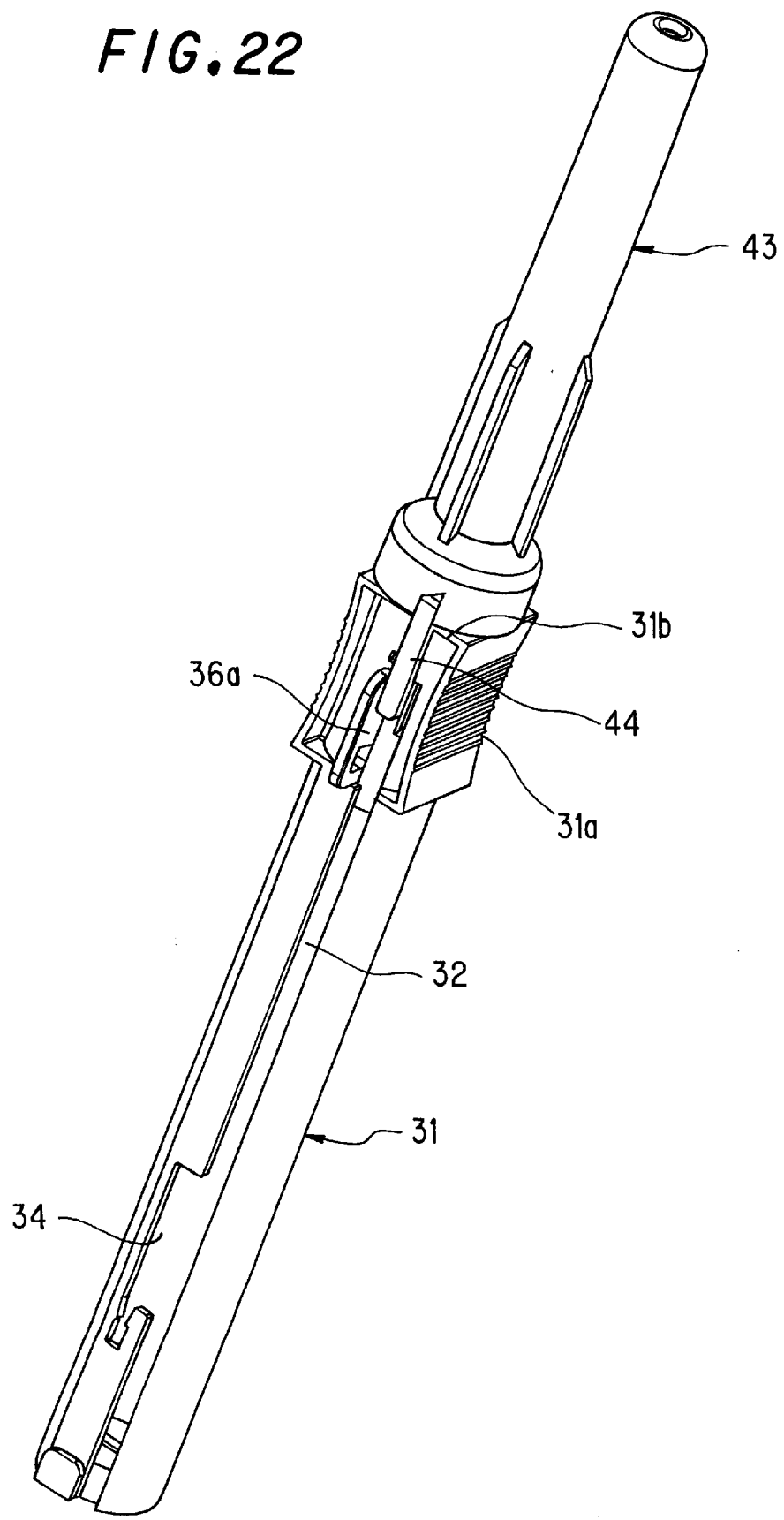
FIG. 22 is a perspective view showing a stored state of a puncturing device with a cap.
Figure 23:
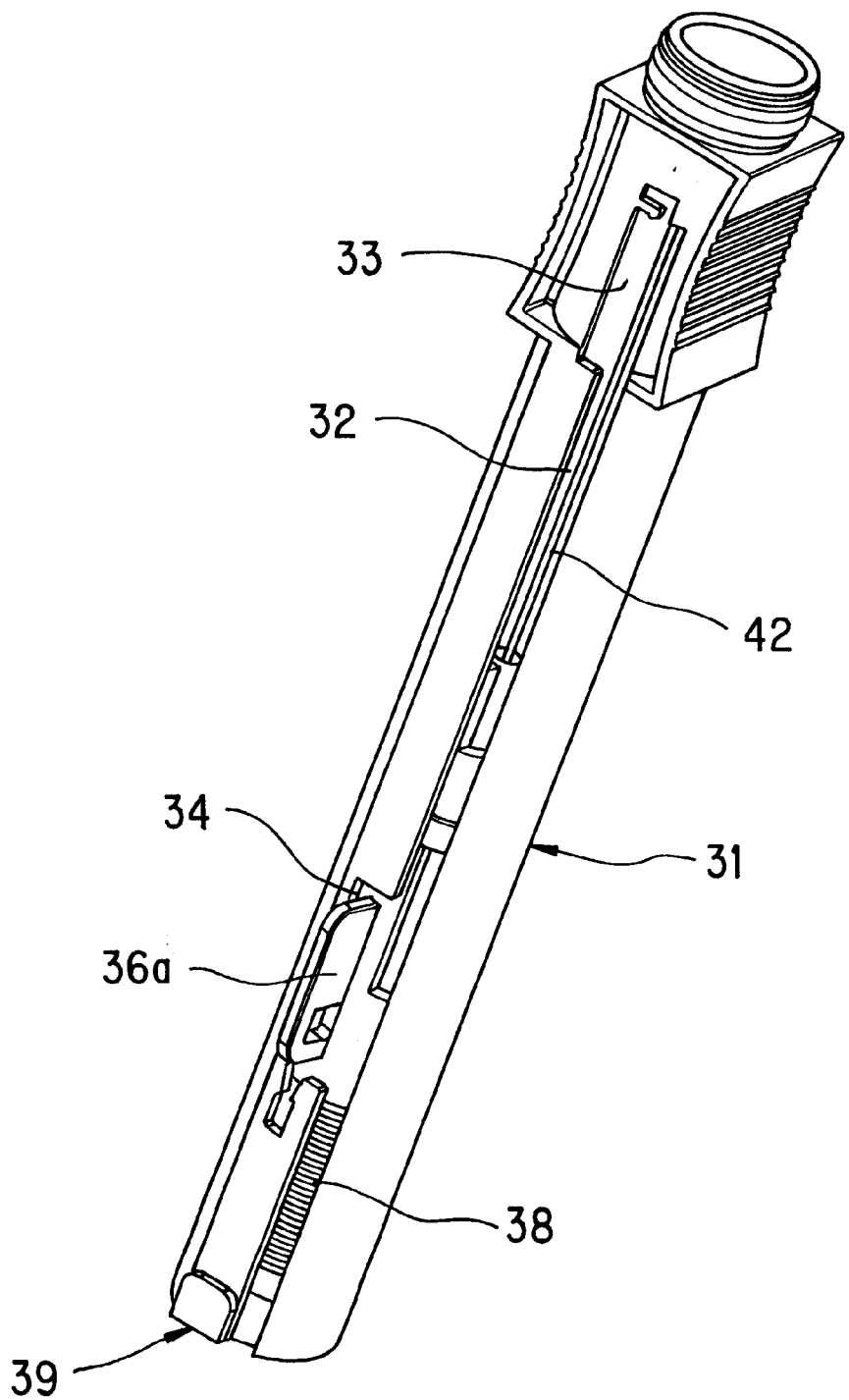
FIG. 23 is a perspective view showing a state where an inner needle is collected in an outer sleeve after use.

As shown in FIG. 22, cap 43 has a bar-shaped stopper 44 on the insertion side thereof. When the cap is fitted, the inner side of stopper 44 abuts the aforementioned flat rim 31b of grip 31a so that cap 43 can be fixed so as not to turn relative to outer sleeve 31 while the side face of stopper 44 substantially abuts the side face of actuator part 36a so that the engagement between actuator part 36a and engagement window 33 will not be disengaged easily even if an external force is applied to actuator part 36a.

The means for stopping the rotation of cap 43 relative to the outer sleeve will not be limited to the above embodiment. That is, any engagement will do which will stop the relative rotation of the inner cap surface to the outer periphery of the attachment of the outer sleeve. Further, the stopper need not be of a bar-shape, but a slot which will have actuator part 36a fitted therein may be formed on the end part on the inserted side.

(The Fourth Embodiment)

Figure 24:
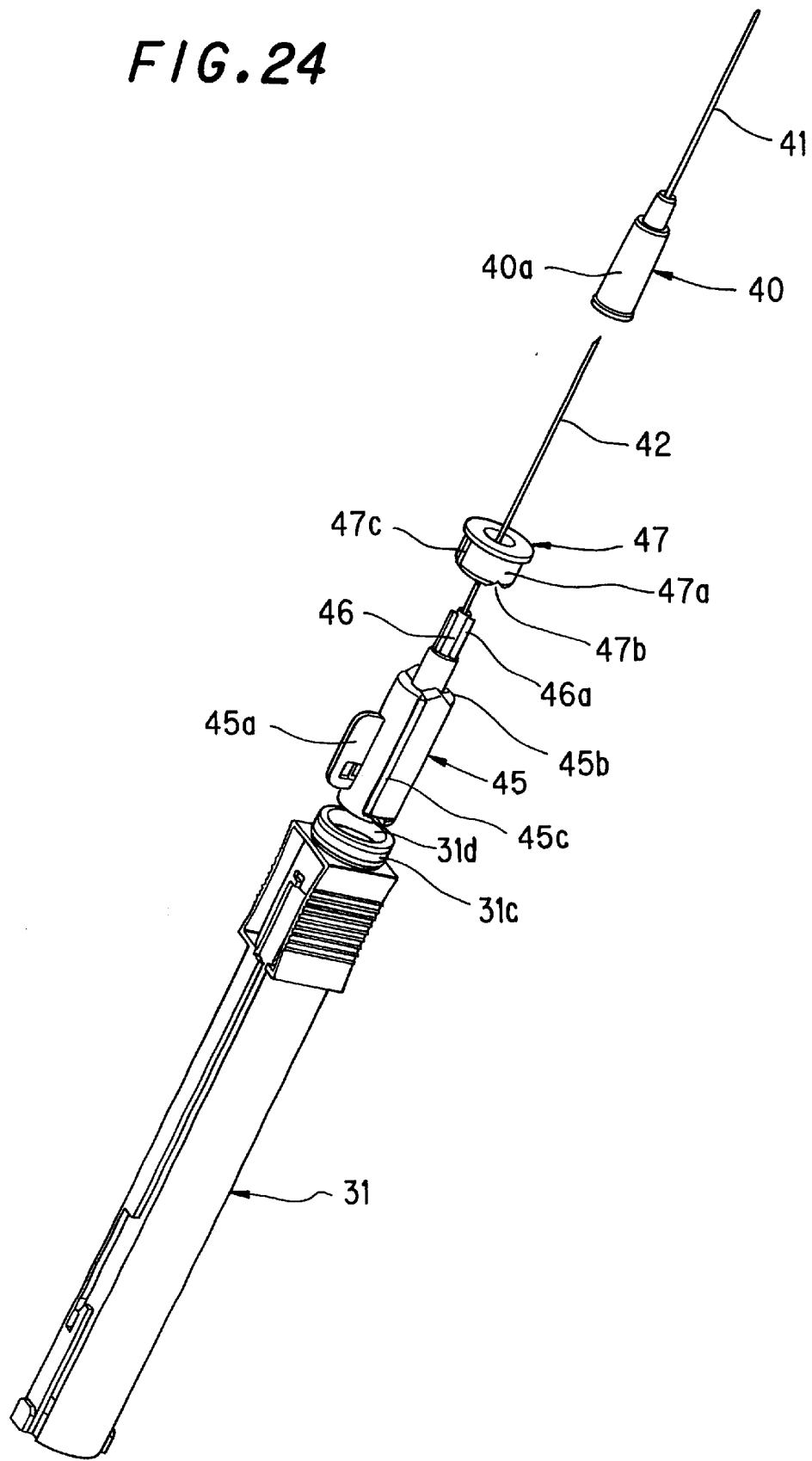
FIG. 24 is an exploded perspective view showing essential components of a puncturing device of the fourth embodiment of the invention.
Figure 25:
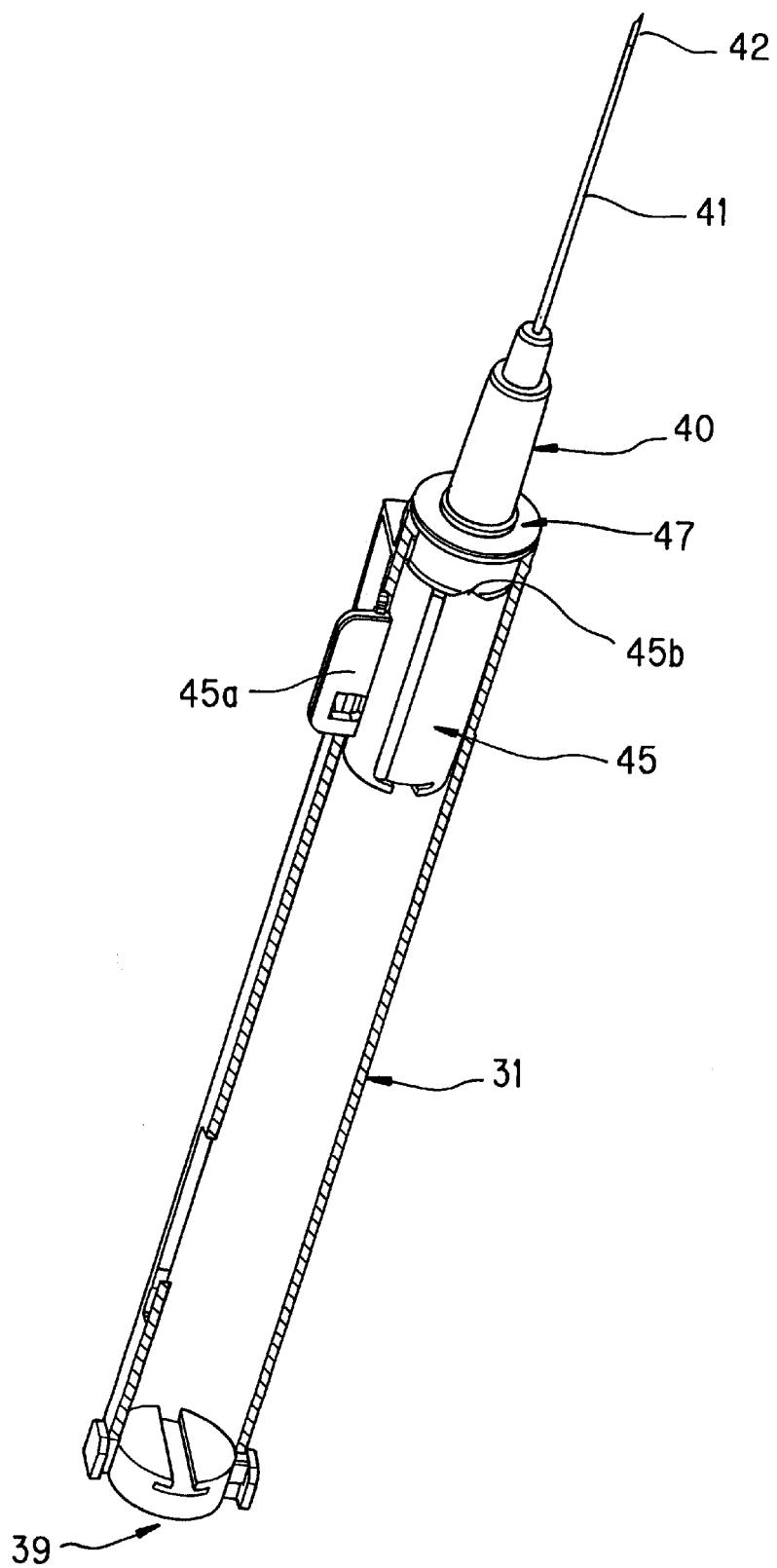
FIG. 25 is a perspective, partially cutaway view showing a state of a puncturing device of the fourth embodiment immediately before its use.
Figure 26:
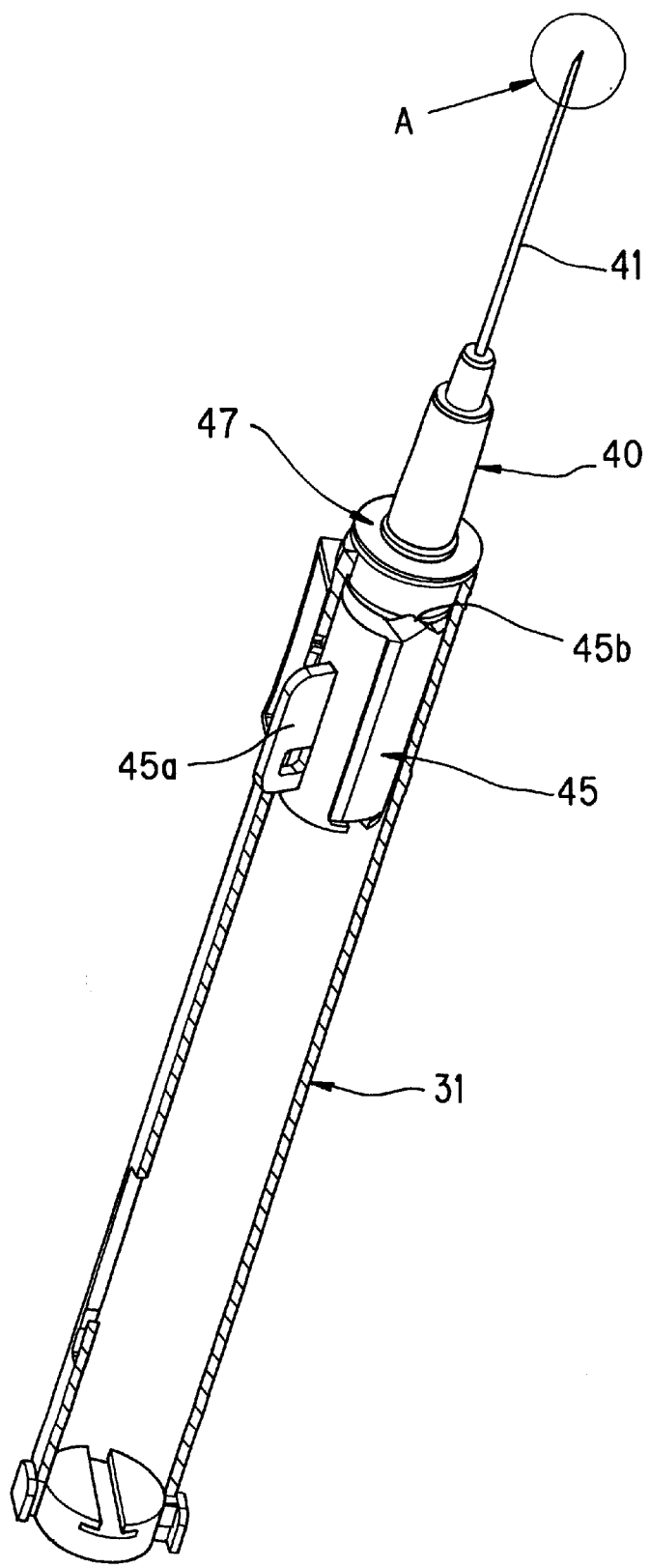
FIG. 26 is a perspective, partially cutaway view showing a state of a puncturing device of the fourth embodiment where an actuator part is rotated for use.

FIGS. 24 through 26 are perspective views showing a puncturing device of the fourth embodiment of the invention.

The basic configuration of the fourth embodiment is almost the same as that of the third embodiment. So only the difference will be described. The same components as in the third embodiment will be allotted with the same reference numerals without description.

First, an actuator 45 has an attachment part 46 at the front part thereof. This attachment part 46 has ribs 46a formed axially extending at appropriate sites on the outer periphery thereof. Actuator 45 further has ribs 45c at appropriate sites in the rear cylindrical portion having a slightly greater diameter and a projected actuator part 45a extending in the axial direction, on one side on the outer periphery thereof. Formed in the front part of the relatively large-diametric rear cylindrical portion is a cam portion 45b having mountain-like projections (the cam shape should not be limited to this).

A movable ring 47 is arranged inside opening 31d. Cylindrical part 47a of movable ring 47 has a rib 47c extending axially on the peripheral thereof, which will mate with an unillustrated groove formed on the inner wall of opening 31d so that movable ring 47 will slide in only the axial direction with respect to outer sleeve 31.

Provided on the rear end of cylindrical part 47a of movable ring 47 is a cam portion 47b having notches which will mate with cam portion 45b formed on actuator 45.

In a state before puncture shown in FIG. 25, cam portion 45b and cam portion 47b engage with each other. When actuator part 45a is turned from this state as shown in FIG. 26, cam portion 45b will disengage from cam portion 47b so as to move movable ring 47 forward (the change of the relationship between the cam portions will make no other difference).

(The Operation of the Third Embodiment)

With the puncturing device of the third embodiment, hard, e.g., metallic, inner needle element 42 to be disposed of after insertion of soft, outer needle element 40 into the human body can be collected instantly inside outer sleeve 31 by a single hand operation by virtue of the restoring force of spring 38. That is, the collection can be done by only rotating actuator part 36a by the fingers relative to outer sleeve 31, so as to bring the actuator part from engagement window 33 of the outer sleeve to guide slot 32.

Immediately before the rotation of actuator part 36a, ribs 37a formed on the attachment part 37 of the actuator engage tightly, due to friction, the inner surface of base part 40a of the outer needle element. As actuator part 36a is rotated, ribs 37a slide with respect to the inner surface of base part 40a so that friction therebetween decreases and cam portion 36e moves movable ring 31e forward to thereby smoothly push outer needle element 40 forward. Therefore, the retention of inner needle 42 within outer needle element 40 is released by the restoring force of spring 38, and hence inner needle 42 is retracted, together with actuator 36, into outer sleeve 31.

In connection with this, it is also possible to provide an active engagement between ribs 37a and the inner surface of base part 40a instead of frictional engagement, so that the engagement will be completely freed when actuator part 36a starts to be rotated.

When, with actuator 36 retracted, actuator part 36a is turned so that it abuts engagement window 34, the outer peripheral portions of ribs 36c abut on, and become engaged with, the flat portions formed on the inner periphery of the outer sleeve so that actuator 36 will be fixed without instability, as in a similar manner to the case where actuator part 36a abuts engagement window 33 as stated above.

In this state, when actuator part 36a is further moved back to fit into fitting slot 34a which is formed further behind engagement window 34, engaging projections fit into engagement window 36b cut through actuator part 36a. That is, since fitting slot 34a has a pair of saw-toothed projections, their perpendicular surfaces engage the rear end of engagement window 36b, thus prohibiting any attempted moving of actuator part 36a forward. In this way, it is possible to restrict the hazardous attempt of reusing the puncturing device after it has been once used.

If spring 38 has been set with a twisting force, the actuator part will automatically become engaged with the engagement window by the restoring force even if the actuator part has been left as it is after the use of the device. This markedly enhances the safety of operations. Since the cap stops the actuator part turning before the use of the puncturing device, there is no concern that the engagement will be released unintentionally by an external force during transport or preparation for use of the puncturing device.

The operation of the fourth embodiment is the same as that of the third embodiment described above.

As already stated above, when the needle is inserted in a weak thin vein such as of a child, there is a risk of the other sidewall of the lumen of the vein being damaged if the puncture is too deep. On the other hand, there is another problem in that a too shallow puncture cannot place the outer needle even though the inner needle has punctured the vein. The operation of the invention to provide countermeasures against these problems will be described next.

Figure 27:
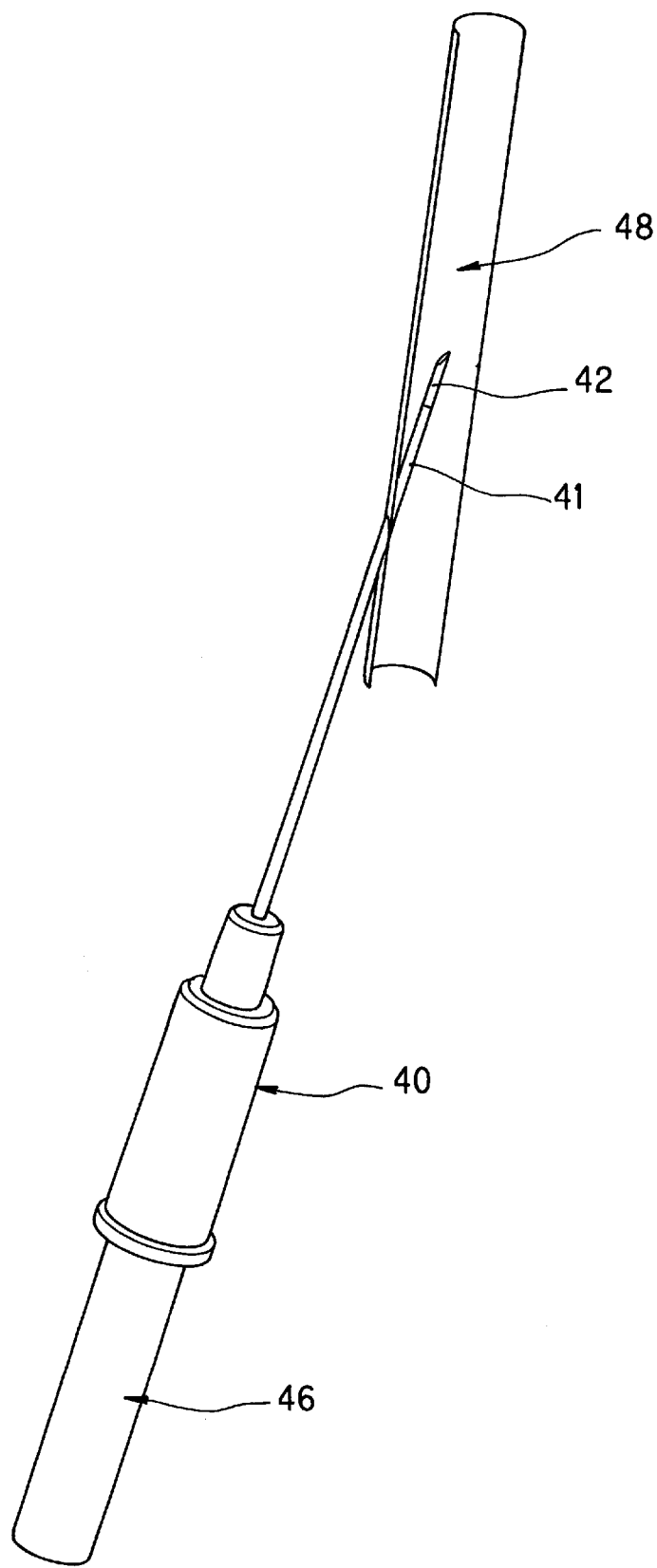
FIG. 27 is an illustrative view showing a state where a needle is correctly inserted into the vein.

First, FIG. 27 shows a state where the needle is correctly punctured into a vein 48. This needs skill.

Figure 28:
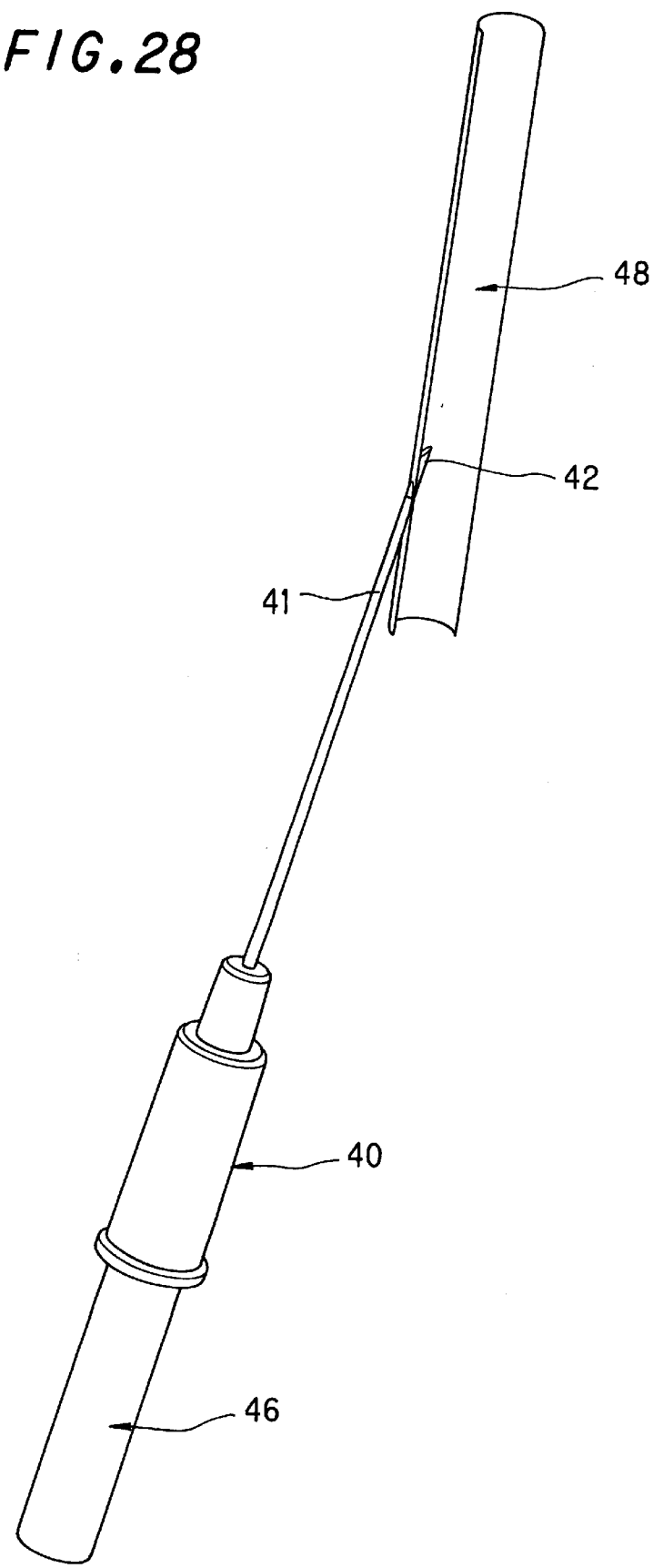
FIG. 28 is an illustrative view showing a state where a needle is incorrectly inserted into the vein.

In the state of FIG. 28 where inner needle 42 has punctured and reaches vein 48, the flow of the blood through inner needle 42 into the actuator can be viewed and hence this state may be erroneously judged to be good. In this case, however, outer needle 41 has not yet reached the inside of vein 48 because of a shallow puncture due to too much cautiousness, resulting in an unsuccessful puncture.

Figure 30:
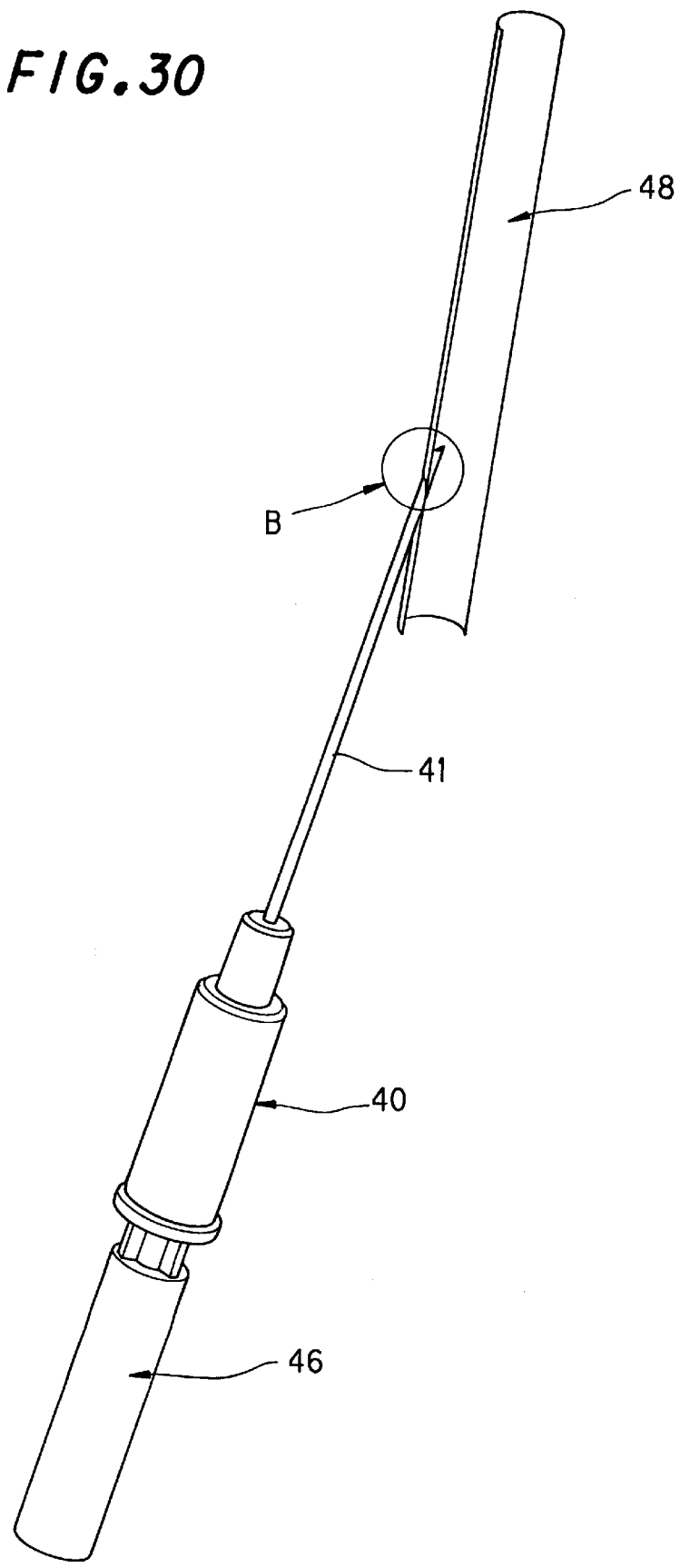
FIG. 30 is an illustrative view showing a state where an outer needle is moved forward after a shallow puncture of the needle into the vein.

However, as shown in FIG. 26, as actuator part 45a is rotated, cam portion 45b moves movable ring 47 forward to smoothly push outer needle element 40 (by about 1 to 1.5 mm). This situation is illustrated in FIG. 30.

Figure 29:
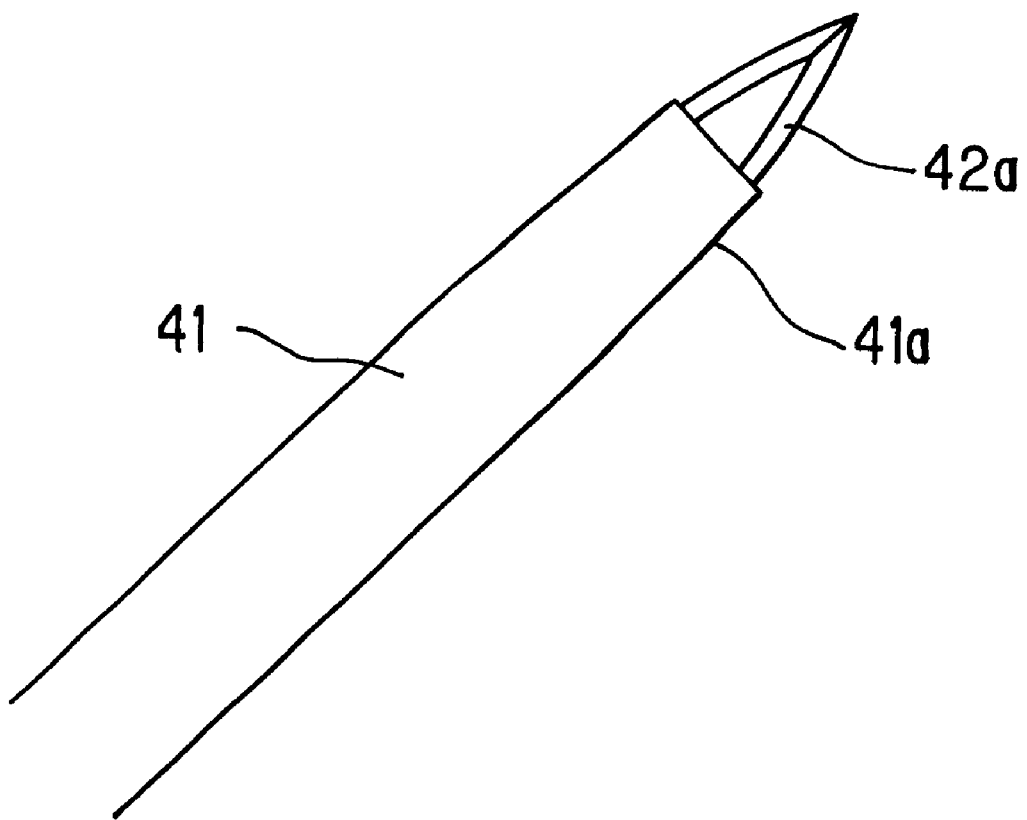
FIG. 29 is an enlarged view of an encircled part A in FIG. 26.
Figure 31:
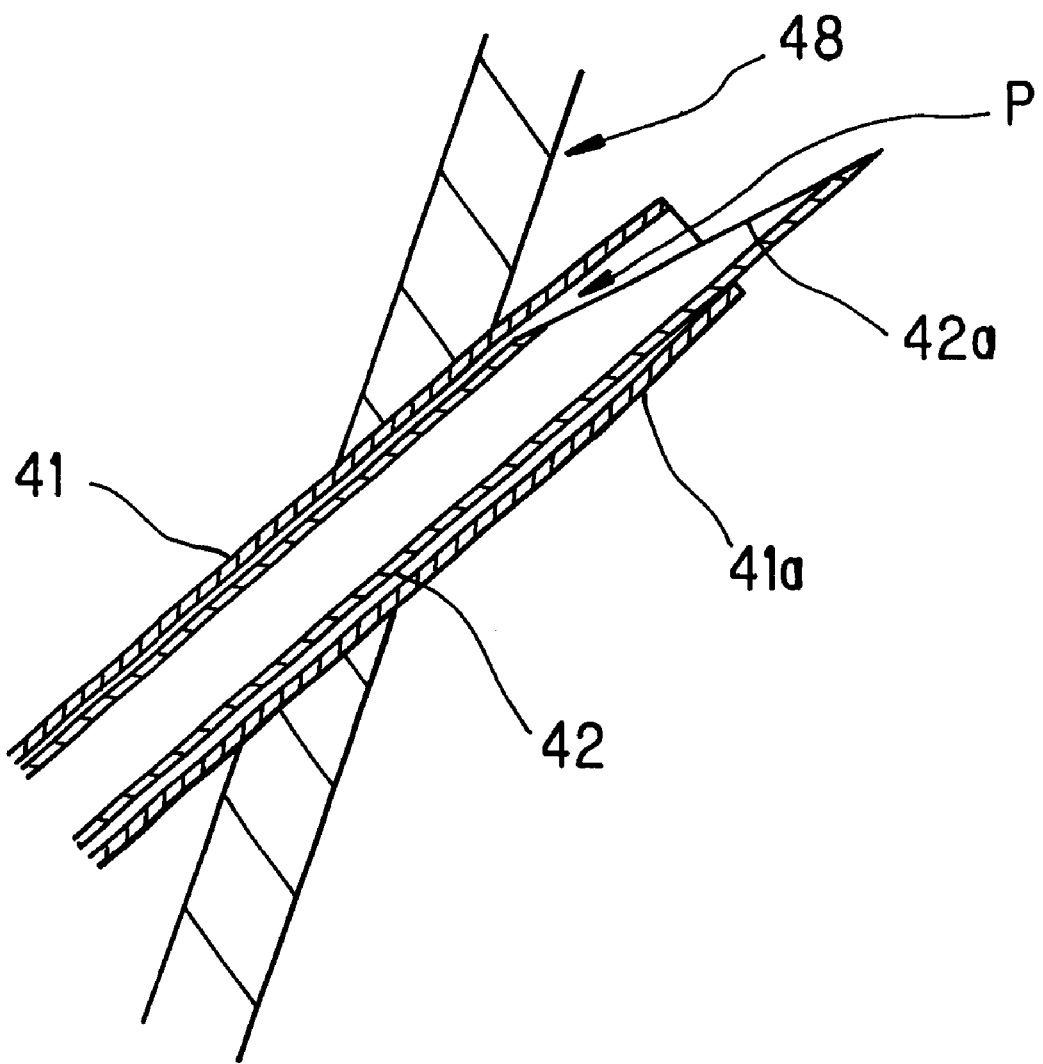
FIG. 31 is an enlarged view of an encircled part B in FIG. 30.

FIG. 29 is an enlarged view of an encircled part A in FIG. 26. FIG. 31 is an enlarged view of an encircled part B in FIG. 30.

As shown in FIG. 31, when outer needle 41 has advanced relative to inner needle 42, tip 41a of the outer needle covers the bevel or cutting edge 42a of the inner needle, in an appropriate manner.

In this condition, an open space is established which communicates with the micro gap between the outer periphery of inner needle 42 and the inner periphery of outer needle 41 so as to allow the blood to enter the gap (in the direction of arrow P). Since this condition can be viewed, it is possible to confirm a correct puncture of outer needle 41 into vein 48. That is, this method enables a correct placement of outer needle 41 by appropriate advancement of outer needle 41 after a safe, not too deep, puncture. For this purpose, the outer sleeve, actuator and outer needle element are configured of a see-through synthetic resin.

At the same time, the retained state of inner needle 42 relative to outer needle element 40 is disengaged by the resorting force of spring 38 so that inner needle 42 retracts together with actuator 45 into outer sleeve 31.

In either the above third or fourth embodiment, movable ring 31e or 47 are interposed to advance outer needle element 40. However, an outer needle element 40 may be formed with a cam portion in its base part whilst its rotation being locked with respect to outer sleeve 31 so as to directly advance outer needle element 40 by the rotation of actuator part 36a or 45a.

Thus, the puncturing device of the invention is configured and operates as above. Therefore, use of this puncturing device allows the needle after use to be collected into the outer sleeve immediately after the application to the human body, by only a simple, single hand operation. As a result, the inner needle, or hard, e.g., metallic, inner needle element can be kept safe, so that it is possible to protect health care workers from needlestick injuries. Further, conventional puncturing devices have been cased merely storage, but a simple package as used with a typical injection needle can be used for the puncturing device of the invention, thus leading to an attainment of a low price. From these viewpoints, the invention is markedly effective in protecting health care workers from secondary infection, which is posing a social problem.

In addition, since the indwelling needle can be fixed during use without instability relative to the outer sleeve and the outer needle element can be easily and reliably inserted and left in the vein after the use, the device can alleviate the burden on the human body and secure its safety.

Since the needle can be prevented from accidentally protruding out and can be prohibited from being reused after it has been once used, the device is extremely safe.

Since the attachment of the spring is simple and hence the assembly is quite simplified, it is possible to produce an inexpensive puncturing device.

The device of the invention makes it possible to insert the needle correctly and safely into a weak, thin vein such as that of a child.

What is claimed is:

1. A medical puncturing device for an indwelling needle, comprising:

an indwelling needle composed of an indwelling outer needle element of a soft synthetic resin capillary tube and a puncturing inner needle element of a metallic capillary tube fitted through the outer needle element;

an outer sleeve for incorporating the indwelling needle and having a guide slot cut along the axial direction on the peripheral surface thereof;

an actuator disposed at the rear end of the indwelling needle and having a projected actuator part fitted through the guide slot; and a spring interposed between the rear end of the actuator and the rear end of the outer sleeve for urging the indwelling needle to the retracted position inside the outer sleeve, wherein the indwelling needle can move in and out through the opening of the outer sleeve by the actuation of the actuator; and the guide slot further has an engagement window formed continuous from the proximity of the front end thereof forming an L-shaped configuration; and the indwelling needle is kept in the projected state with respect to the outer sleeve when the actuator is moved forward and the projected actuator part formed on the actuator is turned so as to be engaged with the engagement window.

2. A puncturing device for an indwelling needle, the device comprising:

an outer sleeve;

an indwelling needle having an indwelling outer needle element formed of a soft synthetic resin capillary tube and disposed at a front end of the outer sleeve and a puncturing inner needle of a hard capillary tube fitted through the outer needle element;

an actuator integrally formed at a rear end of the inner needle and arranged inside the outer sleeve and the actuator having a projected actuator part; and wherein the outer sleeve has a guide slot cut along the axial direction on a peripheral surface thereof and an engagement window formed continuous from a proximity of the front end thereof forming an L-shape configuration, the projected actuator part being fitted through the guide slot, wherein a tip of the inner needle is kept in a projected state from a tip of the outer needle element when the projected actuator part is engaged with the engagement window;

wherein a spring urging the inner needle to the retracted position inside the outer sleeve is provided between the rear end of the actuator and the rear end of the outer sleeve;

wherein the spring exerts twisting force on the actuator so that the actuator turns in the rotational direction, and the actuator is automatically fitted and engaged into the rear engagement window due to the twisting force of the spring when the actuator moves back to the retracted position.

3. The puncturing device according to claim 1 or 2, wherein the actuator part is turned and slidably fitted into the engagement window so as to be engaged therein and in the engaged state, one end of the actuator part is mated with one end of the engagement window forming a disengageable engagement which prevents easy removal of the actuator part from the engagement window.

4. The puncturing device according to claim 1 or 2, wherein the outer sleeve has front and rear engagement windows in L-shaped configurations, one continuous from the proximity of the front end thereof and the other continuous from the proximity of the rear end thereof, and the actuator part is slidably fitted into each engagement window and engaged therein as the actuator part is turned.

5. The puncturing device according to claim 4, wherein when the actuator part is engaged with the rear engagement window, an engaging portion formed at one end of the rear engagement window engages the actuator part so as to prohibit the actuator part from disengaging from the engagement window.

6. The puncturing device according to claim 1 or 2, wherein when the projected actuator part is turned and engaged with the engagement window, abutment portions formed on the inner periphery of the outer sleeve and on the outer periphery of the actuator engage with each other so as to secure the actuator relative to the outer sleeve to thereby fix the indwelling needle without instability.

7. A puncturing device for an indwelling needle, the device comprising:
- an indwelling needle including an indwelling outer needle element formed of a soft synthetic resin capillary tube and having a puncturing inner needle element of a hard capillary tube fitted through the outer needle element;
- an outer sleeve having a guide slot out along the axial direction on the peripheral surface thereof and an engagement window formed continuous from the proximity of the front end thereof forming an L-shaped configuration;
- the inner needle fitted through the outer needle element; and
- an actuator integrally formed at the rear end of the inner needle and arranged inside the outer sleeve and the actuator having an actuator part,
- wherein the indwelling needle is kept in the projected state when the actuator part of the actuator is engaged with the engagement window at the front end, and the outer needle is advanced relative to the inner needle while the inner needle is retracted together with the actuator into the outer sleeve when the actuator part is turned from the L-shaped engagement window to the guide slot side,
- wherein a movable ring which can move only in the axial direction with respect to the outer sleeve is arranged at the front opening of the outer sleeve and in front of the actuator while cam portions are formed on the movable ring and on the actuator, and when the actuator is turned, the movable ring moves forward so that its front end urges the rear end of the outer needle element to advance the outer needle element.

8. The puncturing device according to claim 7, wherein when the outer needle is advanced with respect to the inner needle, a tip of the outer needle covers a beveled cutting edge of the inner needle.

9. The puncturing device of claim 1, wherein the spring exerts twisting force on the actuator so that the actuator turns in the rotational direction, and the actuator is automatically fitted and engaged into the rear engagement window due to the twisting force of the spring when the actuator moves back to the retracted position.

10. The puncturing device according to claim 2, further comprising a rotation stopper between the front end of the outer sleeve and the rear end of the outer needle element.

* * * * *